(12) United States Patent
Wiedemann et al.

(10) Patent No.: US 12,643,902 B2
(45) Date of Patent: Jun. 2, 2026

(54) PROCESS FOR PREPARING ENANTIOMERICALLY ENRICHED SUBSTITUTED PYRROLO[2,3-D]PYRIMIDINES

(71) Applicant: Sun Pharmaceutical Industries, Inc., Princeton, NJ (US)

(72) Inventors: Sean Wiedemann, Burlington, MA (US); Cameron J. Cowden, Lexington, MA (US); Patrick Bazinet, Somerville, MA (US); Kathryn E. Kavouris, Folsom, CA (US); Kuo-Ming Wu, Lexington, MA (US); Robert S. Lewis, Lexington, MA (US)

(73) Assignee: Sun Pharmaceutical Industries, Inc., Princeton, NJ (US)

( * ) Notice: Subject to any disclaimer, the term of this patent is extended or adjusted under 35 U.S.C. 154(b) by 572 days.

(21) Appl. No.: 18/020,869

(22) PCT Filed: Aug. 12, 2021

(86) PCT No.: PCT/US2021/045652

§ 371 (c)(1),
(2) Date: Feb. 10, 2023

(87) PCT Pub. No.: WO2022/036030

PCT Pub. Date: Feb. 17, 2022

(65) Prior Publication Data

US 2023/0322787 A1 Oct. 12, 2023

Related U.S. Application Data

(60) Provisional application No. 63/064,695, filed on Aug. 12, 2020.

(51) Int. Cl.
*C07D 487/04* (2006.01)
*B01J 31/40* (2006.01)

(52) U.S. Cl.
CPC ........ *C07D 487/04* (2013.01); *B01J 31/4046* (2013.01); *C07B 2200/07* (2013.01)

(58) Field of Classification Search
CPC .................................................... C07D 487/04
USPC .......................................................... 544/280
See application file for complete search history.

(56) References Cited

U.S. PATENT DOCUMENTS

| | | | |
|---|---|---|---|
| 9,000,161 | B2 | 4/2015 | Zhou et al. |
| 9,249,149 | B2 | 2/2016 | Silverman et al. |
| 9,662,335 | B2 | 5/2017 | Rodgers et al. |
| 10,561,657 | B2 | 2/2020 | Zhu et al. |
| 10,561,659 | B2 | 2/2020 | Wagner et al. |
| 2021/0387991 | A1 | 12/2021 | Silverman et al. |
| 2022/0213105 | A1 | 7/2022 | Lewis et al. |
| 2022/0306636 | A1 | 9/2022 | Lewis et al. |

FOREIGN PATENT DOCUMENTS

| | | | |
|---|---|---|---|
| CN | 107759623 | A | 3/2018 |
| CN | 107915738 | A | 4/2018 |
| EP | 3398952 | A1 | 11/2018 |
| WO | WO-2007/070514 | A1 | 6/2007 |
| WO | WO-2010/038434 | A1 | 4/2010 |
| WO | WO-2010/083283 | A2 | 7/2010 |
| WO | WO-2013/188783 | A1 | 12/2013 |
| WO | WO-2017/192905 | A1 | 11/2017 |
| WO | WO-2020/163653 | A1 | 8/2020 |
| WO | WO-2021/236139 | A1 | 11/2021 |
| WO | WO-2022/036030 | A1 | 2/2022 |

OTHER PUBLICATIONS

International Search Report and Written Opinion for International Application No. PCT/US2021/045652 dated Oct. 29, 2021.

21.5: Hydrolysis of nitriles <https://chem.libretexts.org/Courses/SUNY_Potsdam/Book%3A_Organic_Chemistry_II_(Walker)/21%3A_Nucleophilic_Addition_of_Weak_Nucleophiles/21.05%3A_Hydrolysis_of_nitriles> Oct. 17, 2023.

Berger et al., "Une Nouvelle Méthode de Saponification des Amides et des Nitriles" vol. 46, No. 8, p. 600-604 (1927).

(Continued)

*Primary Examiner* — Douglas M Willis
(74) *Attorney, Agent, or Firm* — Medler Ferro Woodhouse & Mills PLLC

(57) ABSTRACT

Improved processes for preparing enantiomerically enriched intermediates for the synthesis of ruxolitinib and deuterated forms of ruxolitinib and deuterated analogs of ruxolitinib of Formula I:

Formula I

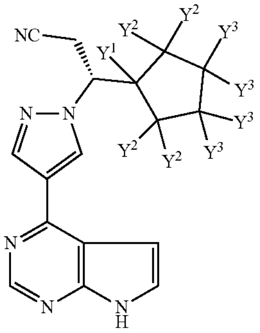

wherein, $Y^1$ is hydrogen or deuterium; each $Y^2$ is the same and is hydrogen or deuterium; and each $Y^3$ is the same and is hydrogen or deuterium are disclosed. Certain aspects are also directed to deuterated intermediates useful in the synthesis of deuterated forms of ruxolitinib. Certain aspects are also directed to reaction mixtures for preparing enantiomerically enriched intermediates useful in the synthesis of ruxolitinib and deuterated forms of ruxolitinib.

10 Claims, No Drawings

(56) References Cited

OTHER PUBLICATIONS

Cason et al., "Branched-Chain Fatty Acids. XXVII. Further Study of the Dependence of Rate of Amide Hydrolysison Substitution Near the Amide Group Relativerates of Hydrolysis of Nitrile to Amide and Amide to Acid" J. Org. Chem. vol. 18, No. 9, p. 1129-1136 (1953).
Hydrolysis of nitriles: Amide vs Carboxylic acid <https://chemistry.stackexchange.com/questions/150031/hydrolysis-of-nitriles-amide-vs-carboxylic-acid> Retrieved on Line Oct. 17, 2023.
International Search Report and Written Opinion for International Application No. PCT/US2020/017093 mailed Apr. 30, 2020.
International Search Report and Written Opinion for International Application No. PCT/US2020/045977 mailed Feb. 5, 2021.
Jensen et al., "Kinetics and Mechanism of Nitrile Hydration Catalyzed by Unhindered Hydridobis (phosphine) platinum (II) Complexes. Regioselective Hydration of Acrylonitrile" J.Am.Chem.Soc, vol. 108, p. 723-729 (1986).
Krieble et al., "The Hydrolysis of Nitriles with Acids" JACS, vol. 61, p. 560-563 (1939).
Magat et al., Acid-catalyzed Reactions of Nitriles. I. The Reaction of Nitriles with Formaldehyde, vol. 73, No. 3, p. 1028-1031 (1951).
Meier, "Triphenylphosphine Hydrobromide" EROS, DOI: 10.1002/047084289X (2001).
Miocque et al., "Addition des reactifs nucléophiles sur la triple liaison nitrile." Ann. Chim , vol. 5, p. 11-22. (1970).
Phind V4 Model <https://www.phind.com/search?cache=mdfsymlxm2bc4omvjmkwpr5t> Retrieved on Line Oct. 17, 2023.
Rabinovitch et al., "The Hydrolysis of Aliphatic Nitriles in Concentrated Hydrochloric Acid Solutions" Canadian Journal of Research, vol. 20b, No. 10 (1942).
Ripin and Evans <http://ccc.chem.pitt.edu/wipf/MechOMs/evans_pKa_table.pdf> Retrieved on Line Oct. 17, 2023.
Shafer, "Nitrile reactivity" The Chemistry of the cyano group, Chapter 6, (1970).
Shiner et al., "Deuterium isotope effects for migrating and nonmigrating groups in the solvolysis of neopentyl-type esters," Journal of the American Chemical Society, 103(2): 436-442 (1981).
Snyder et al., "Polyphosphoric Acid as a Reagent in Organic Chemistry. VI.1 The Hydrolysis of Nitriles to Amides" JACS (1954).
Zhang et al., "An improved synthesis of 4-chloro-7H-pyrrolo[2,3-d]pyrimidine," Chemistry of Heterocyclic Compounds, 54: 638-642 (2018).
Zil'berman, "Reactions of Nitriles With Hydrogen Halides and Nucleophilic Reagents," Russ. Chem. Rev. 31, 615 (1962).

PROCESS FOR PREPARING ENANTIOMERICALLY ENRICHED SUBSTITUTED PYRROLO[2,3-D]PYRIMIDINES

CROSS-REFERENCE TO RELATED APPLICATIONS

This application is the U.S. National Stage of International Application No. PCT/US2021/045652, filed Aug. 12, 2021, which designates the U.S., published in English, and claims the benefit of U.S. Provisional Application No. 63/064,695, filed on Aug. 12, 2020. The entire teachings of the above applications are incorporated herein by reference.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41 (3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56 (6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

Ruxolitinib phosphate is a heteroaryl-substituted pyrrolo[2,3-d]pyrimidine, also known as 3(R)-cyclopentyl-3-[4-(7H-pyrrolo[2,3-d]pyrimidin-4-yl)-1H-pyrazol-1-yl]propanenitrile phosphate, and as (R)-3-(4-(7H-pyrrolo[2,3-d]pyrimidin-4-yl)-1H-pyrazol-1-yl)-3-cyclopentylpropanenitrile phosphate, which inhibits Janus Associated Kinases (JAKs) JAK1 and JAK2. These kinases mediate the signaling of a number of cytokines and growth factors important for hematopoiesis and immune function. JAK signaling involves recruitment of STATs (signal transducers and activators of transcription) to cytokine receptors, activation and subsequent localization of STATs to the nucleus leading to modulation of gene expression.

Three ruxolitinib metabolites in humans have been identified as active as JAK inhibitors, namely those resulting from hydroxylation at the 2-position on the cyclopentyl moiety, hydroxylation at the 3-position on the cyclopentyl moiety, and the ketone resulting from further oxidation at the 3-position on the cyclopentyl moiety. (See Shilling, A. D. et al., Drug Metabolism and Disposition, 2010, 38 (11): 2023-2031; FDA Prescribing Information and US20080312258).

Ruxolitinib phosphate has been approved in the US and Europe for the treatment of myelofibrosis and for the treatment of polycythemia vera. Ruxolitinib is currently in Phase III clinical trials for the treatment of essential thrombocythemia and graft-versus-host disease, in Phase II clinical trials for alopecia areata, cancer-related cachexia, atopic dermatitis, HTLV-1-associated adult T-cell leukemia-lymphoma, hematologic blood cancer, HIV infection, acute lymphocytic leukemia, chronic lymphocytic leukemia, acute myeloid leukemia, chronic myeloid leukemia, Hodgkin's lymphoma, non-Hodgkin's lymphoma, thalassemia, vitiligo, and breast cancer. Deuterated ruxolitinib phosphate is currently in Phase II clinical trials for the treatment of alopecia areata.

Because of the beneficial activities of ruxolitinib and deuterated ruxolitinib analogs, there is a continuing need for improved methods for synthesizing ruxolitinib and deuterated forms thereof.

BRIEF SUMMARY OF THE INVENTION

Certain aspects of the present invention are directed to a process for preparing a compound of Formula I:

Formula I

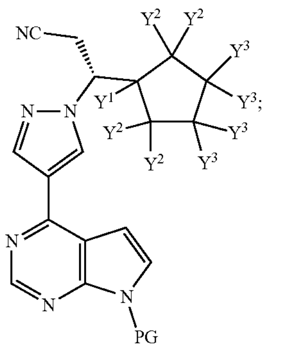

wherein $Y^1$ is hydrogen or deuterium, each $Y^2$ is the same and is hydrogen or deuterium, each $Y^3$ is the same and is hydrogen or deuterium; and PG is hydrogen or a protecting group selected from pivaloyloxymethyl (POM), 2-(trimethylsilyl)ethoxymethyl (SEM), benzyl (Bn), p-methoxybenzyl (PMB), 3,4-dimethoxybenzyl (DMPM), 2,4-dimethoxybenzyl, benzenesulfonyl, tosyl (Ts), t-butoxycarbonyl (BOC), methoxycarbonyl (MOC), benzyloxycarbonyl (CBz), 1-naphthalenesulfonate (1-napsyl), 4-nitrobenzenesulfonyl (p-nosyl), and 2,4,6-trimethylphenylsulfonyl. In some embodiments, the process comprises the step of reacting a compound of Formula II:

Formula II

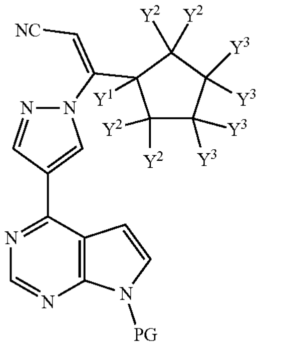

(wherein each of $Y^1$, $Y^2$, $Y^3$, and PG is defined as in Formula I) with hydrogen gas in the presence of a hydrogenation catalyst comprising rhodium and a chiral phosphine ligand (L) according to Formula III:

Formula III

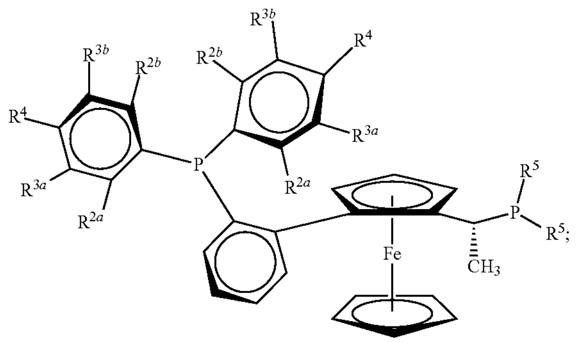

wherein each of $R^{2a}$, $R^{2b}$, $R^{3a}$, $R^{3b}$, and $R^4$ is independently selected from hydrogen, methyl, methoxy, and trifluoromethyl; and $R^5$ is secondary alkyl, tertiary alkyl, or cycloalkyl.

Certain aspects of the present invention are directed to a compound of Formula II; wherein $Y^1$ is hydrogen or deuterium, each $Y^2$ is the same and is hydrogen or deuterium, each $Y^3$ is the same and is hydrogen or deuterium; and PG is hydrogen or a protecting group selected from pivaloyloxymethyl (POM), 2-(trimethylsilyl)ethoxymethyl (SEM), benzyl (Bn), p-methoxybenzyl (PMB), 3,4-dimethoxybenzyl (DMPM), 2,4-dimethoxybenzyl, benzenesulfonyl, tosyl (Ts), t-butoxycarbonyl (BOC), methoxycarbonyl (MOC), benzyloxycarbonyl (CBz), 1-naphthalenesulfonate (1-napsyl), 4-nitrobenzenesulfonyl (p-nosyl), and 2,4,6-trimethylphenylsulfonyl.

Certain aspects of the present invention are directed to a reaction mixture comprising: (a) a compound of Formula II, wherein $Y^1$ is hydrogen or deuterium, each $Y^2$ is the same and is hydrogen or deuterium, each $Y^3$ is the same and is hydrogen or deuterium; and PG is hydrogen or a protecting group selected from pivaloyloxymethyl (POM), 2-(trimethylsilyl)ethoxymethyl (SEM), benzyl (Bn), p-methoxybenzyl (PMB), 3,4-dimethoxybenzyl (DMPM), 2,4-dimethoxybenzyl, benzenesulfonyl, tosyl (Ts), t-butoxycarbonyl (BOC), methoxycarbonyl (MOC), benzyloxycarbonyl (CBz), 1-naphthalenesulfonate (1-napsyl), 4-nitrobenzenesulfonyl (p-nosyl), and 2,4,6-trimethylphenylsulfonyl; (b) a hydrogenation catalyst comprising rhodium and a chiral phosphine ligand (L) according to Formula III, wherein each of $R^{2a}$, $R^{2b}$, $R^{3a}$, $R^{3b}$, and $R^4$ is independently selected from hydrogen, methyl, methoxy, and trifluoromethyl; and $R^5$ is secondary alkyl, tertiary alkyl, or cycloalkyl; and (c) a solvent selected from dichloromethane, tetrahydrofuran, 2-methyltetrahydrofuran, methanol, ethanol, trifluoroethanol, isopropanol, ethyl acetate, isopropyl acetate, and mixtures thereof.

Certain aspects of the present invention are directed to a process for increasing the enantiomeric excess of a compound of Formula I, comprising the steps of: providing a compound of Formula I:

Formula I

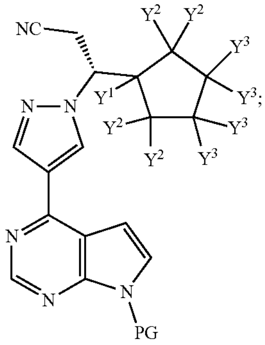

wherein $Y^1$ is hydrogen or deuterium, each $Y^2$ is the same and is hydrogen or deuterium, each $Y^3$ is the same and is hydrogen or deuterium, PG is tosyl (Ts), and having a starting enantiomeric excess of the (R)-enantiomer of at least 70%; dissolving the compound in aqueous ethanol; and crystallizing the compound to provide a final enantiomeric excess of the (R)-enantiomer of at least 98%.

Certain aspects of the present invention are directed to a process for preparing a compound of Formula I, comprising the step of reacting a compound of Formula VII:

Formula VII

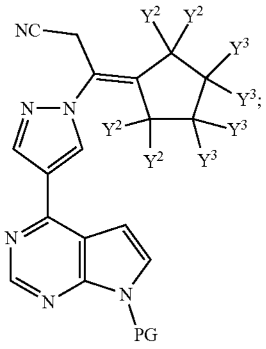

wherein each of $Y^2$, $Y^3$, and PG is defined as in Formula I; with hydrogen gas in the presence of a hydrogenation catalyst comprising rhodium and a chiral phosphine ligand (L) according to Formula VI or Formula VIII:

Formula VI

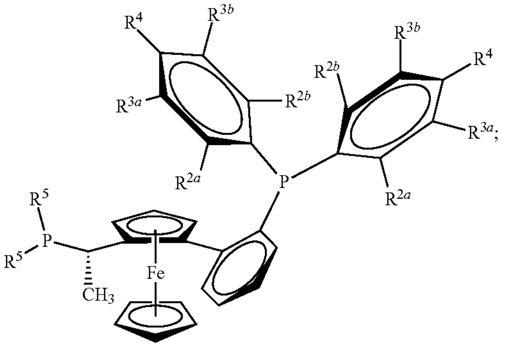

wherein each of $R^{2a}$, $R^{2b}$, $R^{3a}$, $R^{3b}$, and $R^4$ is independently selected from hydrogen, methyl, methoxy, and trifluoromethyl; and $R^5$ is phenyl; or Formula VIII

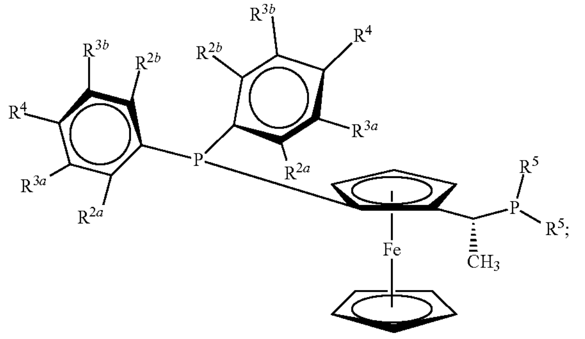

wherein each of $R^{2a}$, $R^{2b}$, $R^{3a}$, $R^{3b}$, and $R^4$ is independently selected from hydrogen, methyl, methoxy, and trifluoromethyl; and $R^5$ is tert-butyl.

Certain aspects of the present invention are directed to a compound of Formula VII, wherein each $Y^2$ is the same and is hydrogen or deuterium, each $Y^3$ is the same and is hydrogen or deuterium; and PG is hydrogen or a protecting group selected from pivaloyloxymethyl (POM), 2-(trimethylsilyl)ethoxymethyl (SEM), benzyl (Bn), p-methoxybenzyl (PMB), 3,4-dimethoxybenzyl (DMPM), 2,4-dimethoxybenzyl, benzenesulfonyl, tosyl (Ts), t-butoxycarbonyl (BOC), methoxycarbonyl (MOC), benzyloxycarbonyl (CBz), 1-naphthalenesulfonate (1-napsyl), 4-nitrobenzenesulfonyl (p-nosyl), and 2,4,6-trimethylphenylsulfonyl.

Certain aspects of the present invention are directed to a reaction mixture comprising:

a. a compound of Formula VII:

Formula VII

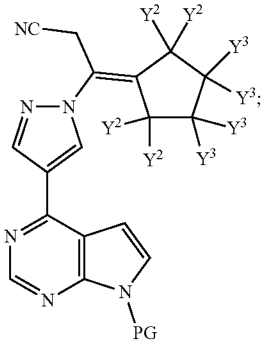

wherein each $Y^2$ is the same and is hydrogen or deuterium, each $Y^3$ is the same and is hydrogen or deuterium; and PG is hydrogen or a protecting group selected from pivaloyloxymethyl (POM), 2-(trimethylsilyl)ethoxymethyl (SEM), benzyl (Bn), p-methoxybenzyl (PMB), 3,4-dimethoxybenzyl (DMPM), 2,4-dimethoxybenzyl, benzenesulfonyl, tosyl (Ts), t-butoxycarbonyl (BOC), methoxycarbonyl (MOC), benzyloxycarbonyl (CBz), 1-naphthalenesulfonate (1-napsyl), 4-nitrobenzenesulfonyl (p-nosyl), and 2,4,6-trimethylphenylsulfonyl;

b. a hydrogenation catalyst comprising rhodium and a chiral phosphine ligand (L) according to Formula VI or Formula VIII:

Formula VI

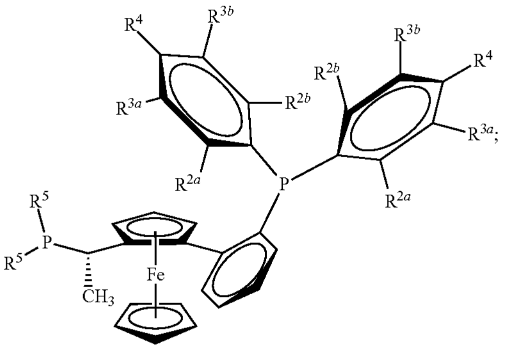

wherein each of $R^{2a}$, $R^{2b}$, $R^{3a}$, $R^{3b}$, and $R^4$ is independently selected from hydrogen, methyl, methoxy, and trifluoromethyl; and $R^5$ is phenyl; or Formula VIII

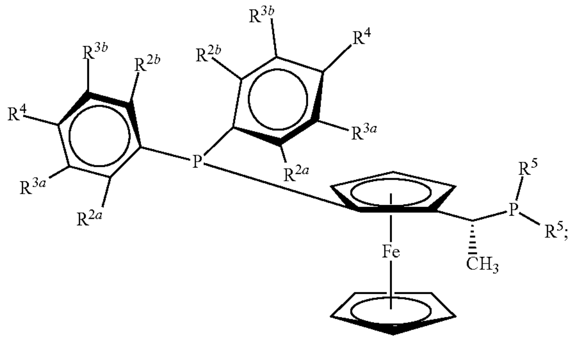

wherein each of $R^{2a}$, $R^{2b}$, $R^{3a}$, $R^{3b}$, and $R^4$ is independently selected from hydrogen, methyl, methoxy, and trifluoromethyl; and $R^5$ is tert-butyl; and c. a solvent selected from dichloromethane, tetrahydrofuran, 2-methyltetrahydrofuran, methanol, ethanol, trifluoroethanol, isopropanol, ethyl acetate, isopropyl acetate, and mixtures thereof.

DETAILED DESCRIPTION OF THE INVENTION

Definitions

The term "alkyl" refers to a monovalent saturated hydrocarbon group. $C_1$-$C_6$ alkyl is an alkyl having from 1 to 6 carbon atoms. In some embodiments, an alkyl may be linear or branched. In some embodiments, an alkyl may be primary, secondary, or tertiary. Non-limiting examples of alkyl groups include methyl; ethyl; propyl, including n-propyl and isopropyl; butyl, including n-butyl, isobutyl, sec-butyl, and t-butyl; pentyl, including, for example, n-pentyl, isopentyl, and neopentyl; and hexyl, including, for example, n-hexyl and 2-methylpentyl. Non-limiting examples of primary alkyl groups include methyl, ethyl, n-propyl, n-butyl, n-pentyl, and n-hexyl. Non-limiting examples of secondary alkyl groups include isopropyl, sec-butyl, and 2-methylpentyl. Non-limiting examples of tertiary alkyl groups include t-butyl.

Unless otherwise specified, "alkylene" by itself or as part of another substituent refers to a saturated straight-chain or branched divalent group having the stated number of carbon atoms and derived from the removal of two hydrogen atoms from the corresponding alkane. Examples of straight chained and branched alkylene groups include $—CH_2$-(methylene), $—CH_2—CH_2$-(ethylene), $—CH_2—CH_2—CH_2$-(propylene), $—C(CH_3)_2—$, $—CH_2—CH(CH_3)—$, $—CH_2—CH_2—CH_2—CH_2$-(butylene), $—CH_2—CH(CH_3)—CH_2—$, $—CH_2—CH_2—CH_2—CH_2—CH_2$-(pentylene), and $—CH_2—C(CH_3)_2—CH_2—$.

The term "alkenyl" refers to a monovalent unsaturated hydrocarbon group where the unsaturation is represented by a double bond. $C_2$-$C_6$ alkenyl is an alkenyl having from 2 to 6 carbon atoms. An alkenyl may be linear or branched. Examples of alkenyl groups include $CH_2═CH—$ (vinyl), $CH_2═C(CH_3)—$, $CH_2—CH—CH_2—$ (allyl), $CH_3—CH═CH—CH_2—$ (crotyl), $CH_3—CH═C(CH_3)—$ and $CH_3—CH═CH—CH(CH_3)—CH_2—$. Where double bond stereoisomerism is possible, the stereochemistry of an alkenyl may be (I), (Z), or a mixture thereof.

The term "alkynyl" refers to a monovalent unsaturated hydrocarbon group where the unsaturation is represented by a triple bond. $C_2$-$C_6$ alkynyl is an alkynyl having from 2 to 6 carbon atoms. An alkynyl may be linear or branched. Examples of alkynyl groups include $HC≡C—$, $CH_3—C≡C—$, $CH_3—C≡C—CH_2—$, $CH_3—C≡C—CH_2—CH_2—$ and $CH_3—C≡C—CH(CH_3)—CH_2—$.

The term "cycloalkyl" refers to a monocyclic or bicyclic monovalent saturated or non-aromatic unsaturated hydrocarbon ring system. The term "$C_3$-$C_{10}$ cycloalkyl" refers to a cycloalkyl wherein the number of ring carbon atoms is from 3 to 10. Examples of $C_3$-$C_{10}$ cycloalkyl include $C_3$-$C_6$ cycloalkyl. Bicyclic ring systems include fused, bridged, and spirocyclic ring systems. Non-limiting examples of cycloalkyl groups include cyclopropyl, cyclobutyl, cyclopentyl, cyclohexyl, cycloheptyl, cis- and trans-decalinyl, norbornyl, and spiro[4.5]decanyl.

The term "carbocyclyl" refers to a monocyclic or bicyclic monovalent saturated or non-aromatic unsaturated hydrocarbon ring system. The term "$C_3$-$C_{10}$ carbocyclyl" refers to a carbocyclyl wherein the number of ring carbon atoms is from 3 to 10. Examples of $C_3$-$C_{10}$ carbocyclyl include $C_3$-$C_6$ carbocyclyl. Bicyclic ring systems include fused, bridged, and spirocyclic ring systems. More particular examples of carbocyclyl groups include, cyclopropyl, cyclobutyl, cyclopentyl, cyclopentenyl, cyclohexyl, cyclohexenyl, cycloheptyl, cis- and trans-decalinyl, norbornyl, norbornenyl, and spiro[4.5]decanyl.

The term "heterocycloalkyl" refers to a monocyclic or bicyclic monovalent saturated or non-aromatic unsaturated ring system wherein from 1 to 4 ring atoms are heteroatoms independently selected from the group consisting of O, N and S. The term "3 to 10-membered heterocycloalkyl" refers to a heterocycloalkyl wherein the number of ring atoms is from 3 to 10. Examples of 3 to 10-membered heterocycloalkyl include 3 to 6-membered heterocycloalkyl. Bicyclic ring systems include fused, bridged, and spirocyclic ring systems. More particular examples of heterocycloalkyl groups include azepanyl, azetidinyl, aziridinyl, imidazolidinyl, morpholinyl, oxazolidinyl, oxazolidinyl, piperazinyl, piperidinyl, pyrazolidinyl, pyrrolidinyl, quinuclidinyl, and thiomorpholinyl.

In the above heterocycloalkyl substituents, the nitrogen, phosphorus, carbon or sulfur atoms can be optionally oxidized to various oxidation states. In a specific example, the group —$S(O)_{0-2}$—, refers to —S-(sulfide), —S(O)-(sulfoxide), and —$SO_2$-(sulfone) respectively. For convenience, nitrogens, particularly but not exclusively, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms can be optionally quaternized; and the ring substituent can be partially or fully saturated or aromatic.

"Aryl" by itself or as part of another substituent refers to a monocyclic or polycyclic monovalent aromatic hydrocarbon group having the stated number of carbon atoms (i.e., $C_5$-$C_{14}$ means from 5 to 14 carbon atoms). Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octophene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthylene, and the like. In a specific embodiment, the aryl group is cyclopentadienyl, phenyl or naphthyl. In a more specific embodiment, the aryl group is phenyl or naphthyl.

"Arylalkyl" by itself or as part of another substituent refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. In one embodiment, the alkyl moiety of the arylalkyl group is ($C_1$-$C_6$) and the aryl moiety is ($C_5$-$C_{14}$). In a more specific embodiment the alkyl group is ($C_1$-$C_3$) and the aryl moiety is ($C_5$-$C_{10}$), such as ($C_6$-$C_{10}$).

The term "heteroaryl" refers to a monocyclic or polycyclic (e.g., having 2, 3, or 4 fused rings) aromatic hydrocarbon ring system, wherein at least one ring atom is a heteroatom independently selected from the group consisting of O, N and S. In some embodiments, the heteroaryl group has 1 or 2 rings. When the heteroaryl group contains more than one heteroatom ring member, the heteroatoms may be the same or different. Nonlimiting examples of heteroaryl groups include without limitation, pyrrolopyrimidinyl, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. The term 5-membered heteroaryl refers to a heteroaryl wherein the number of ring atoms is 5. Nonlimiting examples of 5-membered heteroaryl groups include pyrrolyl, pyrazolyl, oxazolyl, isoxazolyl, thiazolyl, isothiazolyl, oxadiazolyl, thiadiazolyl, furazanyl, imidazolinyl, and triazolyl.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. In one embodiment, the alkyl moiety of the heteroarylalkyl is ($C_1$-$C_6$)alkyl and the heteroaryl moiety is a 5-14-membered heteroaryl. In a more specific embodiment, the alkyl moiety is ($C_1$-$C_3$)alkyl and the heteroaryl moiety is a 5-10 membered heteroaryl.

"Halogen" or "Halo" by themselves or as part of another substituent refers to fluorine, chlorine, bromine and iodine, or fluoro, chloro, bromo and iodo.

It will be recognized that some variation of natural isotopic abundance occurs in a synthesized compound depending upon the origin of chemical materials used in the synthesis. Thus, a preparation of compounds disclosed herein will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. In some embodiments, when a position is designated specifically as "H" or "hydrogen", the position is at least 90%, at least 95%, at least 96%, at least 97%, at least 98%, or at least 99% hydrogen. In some embodiments, when a position is designated specifically as "H" or "hydrogen", the position incorporates ≤10% deuterium, ≤5% deuterium, ≤4% deuterium, ≤3% deuterium, ≤2% deuterium, or ≤1% deuterium. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In some embodiments, a compound of this invention has deuterium incorporation at each designated deuterium atom of at least 52.5%. In some embodiments, a compound of this invention has deuterium incorporation at each designated deuterium atom at least 60%. In some embodiments, a compound of this invention has deuterium incorporation at each designated deuterium atom of at least 67.5%. In some embodiments, a compound of this invention has deuterium incorporation at each designated deuterium atom of at least 75%. In some embodiments, a compound of this invention has deuterium incorporation at each designated deuterium atom of at least 82.5%. In some embodiments, a compound of this invention has deuterium incorporation at each designated deuterium atom of at least 90%. In some embodiments, a compound of this invention has deuterium incorporation at each designated deuterium atom of at least 95%.

In some embodiments, a compound of this invention has deuterium incorporation at each designated deuterium atom of at least 97%. In some embodiments, in a compound of this invention, each designated deuterium atom has deuterium incorporation of at least 98%. In some embodiments, a compound of this invention has deuterium incorporation at each designated deuterium atom of at least 99%. In some embodiments, a compound of this invention has deuterium incorporation at each designated deuterium atom of at least 99.5%.

The term "isotopologue" refers to a molecule in which the chemical structure differs from another molecule of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure will contain molecules having deuterium at each of the positions designated as deuterium in the chemical structure, and may also contain isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. In certain embodiments, the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

As used herein, the term "reacting" is used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Adjustments to the protecting groups and formation and cleavage methods described herein may be adjusted as necessary in light of the various substituents.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, 1-butyl methyl ether, mixtures thereof.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, 1-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, and mixtures thereof.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2 (1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide (DMSO), propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, hexamethylphosphoramide, and mixtures thereof.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, naphthalene, and mixtures thereof.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.).

The reactions of the processes described herein can be carried out in air or under an inert atmosphere. Typically, reactions containing reagents or products that are substantially reactive with air can be carried out using air-sensitive synthetic techniques that are well known to the skilled artisan.

Examples of acids can be inorganic or organic acids. Non-limiting examples of inorganic acids include hydrochloric acid, hydrobromic acid, sulfuric acid, phosphoric acid, and nitric acid. Non-limiting examples of organic acids include formic acid, acetic acid, propionic acid, butanoic acid, benzoic acid, 4-nitrobenzoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Non-limiting examples of bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

Upon carrying out preparation of compounds according to the processes described herein, the usual isolation and purification operations such as concentration, filtration, extraction, solid-phase extraction, recrystallization, chromatography, and the like may be used to isolate the desired products.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present invention also includes salt forms of the compounds described herein. A salt of a compound of this invention is formed between an acid and a basic group of the compound, such as an amino functional group, or a base and an acidic group of the compound, such as a carboxyl functional group. According to one embodiment, the compound is a pharmaceutically acceptable acid addition salt. In one embodiment the acid addition salt may be a deuterated acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid. In one embodiment, the acids commonly employed to form pharmaceutically acceptable salts include the above-listed inorganic acids, wherein at least one hydrogen is replaced with deuterium.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "Sec" or "s-" each refer to secondary. "n-" refers to normal. "i-" refers to iso. "US" refers to the United States of America.

"Substituted with deuterium" refers to the replacement of one or more hydrogen atoms with a corresponding number of deuterium atoms.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Processes

Certain aspects of the present invention are directed to processes of synthesizing compounds of Formula I, which are useful as JAK inhibitors or are intermediates that will be useful as JAK inhibitors after one or more further synthetic steps. In some embodiments, the process comprises an asymmetric hydrogenation which produces an enantiomeric excess of the (R)-enantiomer of the JAK inhibitor or intermediate thereof. Certain embodiments comprise a compound of Formula I, wherein PG is hydrogen, prepared by any process disclosed herein. Certain embodiments comprise CTP-543 prepared by any process disclosed herein for preparing a compound of Formula I.

Some exemplary embodiments comprise a process for preparing a compound of Formula I:

Formula I

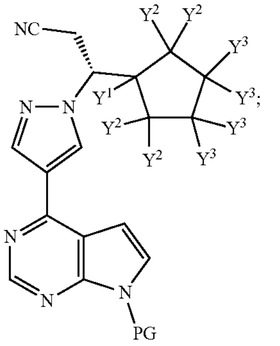

wherein $Y^1$ is hydrogen or deuterium, each $Y^2$ is the same and is hydrogen or deuterium, each $Y^3$ is the same and is hydrogen or deuterium; and PG is hydrogen or a protecting group selected from pivaloyloxymethyl (POM), 2-(trimethylsilyl)ethoxymethyl (SEM), benzyl (Bn), p-methoxybenzyl (PMB), 3,4-dimethoxybenzyl (DMPM), 2,4-dimethoxybenzyl, benzenesulfonyl, tosyl (Ts), t-butoxycarbonyl (BOC), methoxycarbonyl (MOC), benzyloxycarbonyl (CBz), 1-naphthalenesulfonate (1-napsyl), 4-nitrobenzenesulfonyl (p-nosyl), and 2,4,6-trimethylphenylsulfonyl. In some embodiments, PG is hydrogen. In some embodiments, PG is tosyl. In some embodiments, the process comprises the step of reacting a compound of Formula II:

Formula II

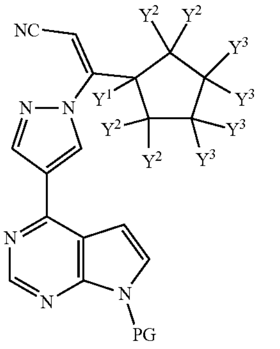

(wherein each of $Y^1$, $Y^2$, $Y^3$, and PG is defined as in Formula I) with hydrogen gas in the presence of a hydrogenation catalyst comprising rhodium and a chiral phosphine ligand (L) according to Formula III:

Formula III

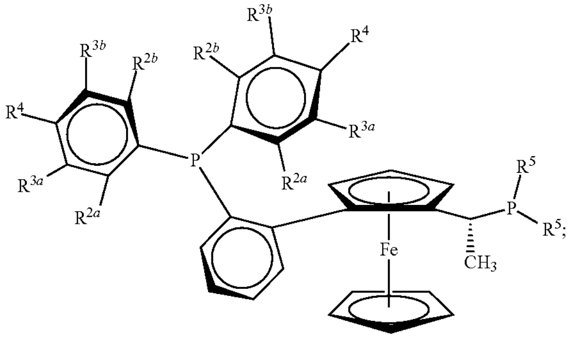

wherein each of $R^{2a}$, $R^{2b}$, $R^{3a}$, $R^{3b}$, and $R^4$ is independently selected from hydrogen, methyl, methoxy, and trifluoromethyl; and $R^5$ is secondary alkyl, tertiary alkyl, or cycloalkyl.

In some embodiments, the process for preparing a compound of Formula I comprises the step of reacting a compound of Formula V:

Formula V

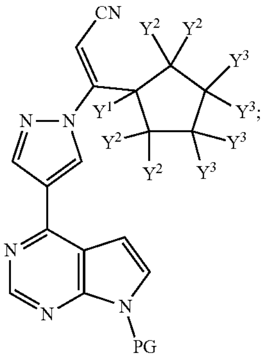

(wherein each of $Y^1$, $Y^2$, $Y^3$, and PG is defined as in Formula I) with hydrogen gas in the presence of a hydrogenation catalyst comprising rhodium and a chiral phosphine ligand (L') according to Formula VI:

Formula VI

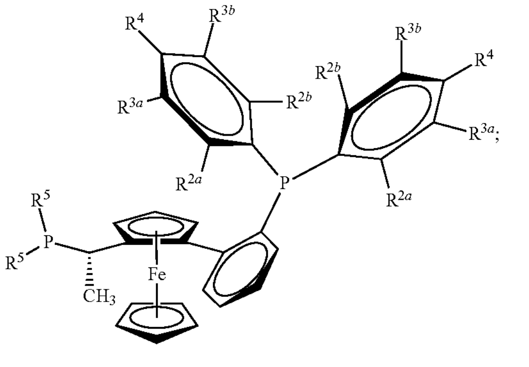

wherein each of $R^{2a}$, $R^{2b}$, $R^{3a}$, $R^{3b}$, and $R^4$ is independently selected from hydrogen, methyl, methoxy, and trifluoromethyl; and $R^5$ is secondary alkyl, tertiary alkyl, or cycloalkyl.

In some embodiments, the process for preparing a compound of Formula I comprises the step of reacting a compound of Formula VII:

Formula VII

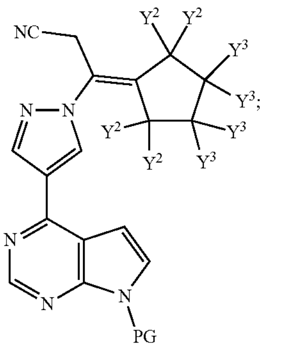

wherein each of $Y^2$, $Y^3$, and PG is defined as in Formula I; with hydrogen gas in the presence of a hydrogenation catalyst comprising rhodium and a chiral phosphine ligand (L') according to Formula VI or (L") according to Formula VIII:

Formula VI

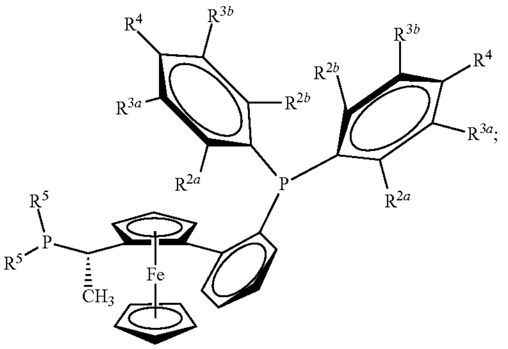

wherein each of $R^{2a}$, $R^{2b}$, $R^{3a}$, $R^{3b}$, and $R^4$ is independently selected from hydrogen, methyl, methoxy, and trifluoromethyl; and $R^5$ is phenyl; or Formula VIII

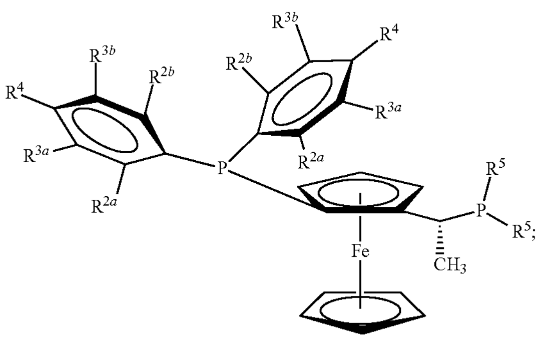

wherein each of $R^{2a}$, $R^{2b}$, $R^{3a}$, $R^{3b}$, and $R^4$ is independently selected from hydrogen, methyl, methoxy, and trifluoromethyl; and $R^5$ is tert-butyl.

In some embodiments, PG is pivaloyloxymethyl (POM). In some embodiments, PG is 2-(trimethylsilyl)ethoxymethyl (SEM). In some embodiments, PG is hydrogen. In some embodiments, PG is tosyl.

In some embodiments of the formulas described herein, each of $Y^1$, $Y^2$, and $Y^3$ is hydrogen. In some embodiments, each of $Y^1$, $Y^2$, and $Y^3$ is deuterium. In some embodiments, $Y^1$ is hydrogen and each of $Y^2$ and $Y^3$ is deuterium. In some embodiments, each of $Y^1$ and $Y^2$ is hydrogen and each of $Y^3$ is deuterium. In some embodiments, each of $Y^1$ and $Y^3$ is hydrogen and each of $Y^2$ is deuterium. In some embodiments, $Y^1$ is at least 95% hydrogen. In some embodiments, $Y^1$ is at least 96% hydrogen. In some embodiments, $Y^1$ is at least 97% hydrogen. In some embodiments, $Y^1$ is at least 98% hydrogen. In some embodiments, $Y^1$ is at least 99% hydrogen.

In some embodiments of Formula VII, each of $Y^2$ and $Y^3$ is deuterium. In some embodiments, each of $Y^2$ is deuterium and each of $Y^3$ is hydrogen. In some embodiments, each of $Y^2$ is hydrogen and each of $Y^3$ is deuterium.

In some embodiments, the process for preparing a compound of Formula I comprises the step of reacting a mixture comprising a mole ratio of ≥80% of a compound of Formula II as disclosed herein to ≤20% of a compound of Formula V as disclosed herein with hydrogen gas in the presence of a hydrogenation catalyst comprising rhodium and a chiral phosphine ligand (L) according to Formula III as disclosed herein. In some embodiments, the process comprises the step of reacting a mixture comprising a mole ratio of ≥90% of a compound of Formula II as disclosed herein to ≤10% of a compound of Formula V as disclosed herein with hydrogen gas in the presence of a hydrogenation catalyst comprising rhodium and a chiral phosphine ligand (L) according to Formula III as disclosed herein. In some embodiments, the process comprises the step of reacting a mixture comprising a mole ratio of ≥95% of a compound of Formula II as disclosed herein to ≤5% of a compound of Formula V as disclosed herein with hydrogen gas in the presence of a hydrogenation catalyst comprising rhodium and a chiral phosphine ligand (L) according to Formula III as disclosed herein.

In some embodiments, the process for preparing a compound of Formula I comprises the step of reacting a mixture comprising a mole ratio of ≥80% of a compound of Formula V as disclosed herein to ≤20% of a compound of Formula II as disclosed herein with hydrogen gas in the presence of a hydrogenation catalyst comprising rhodium and a chiral phosphine ligand (L') according to Formula VI as disclosed herein. In some embodiments, the process comprises the step of reacting a mixture comprising mole ratio of ≥90% of a compound of Formula V as disclosed herein to ≤10% of a compound of Formula II as disclosed herein with hydrogen gas in the presence of a hydrogenation catalyst comprising rhodium and a chiral phosphine ligand (L') according to Formula VI as disclosed herein. In some embodiments, the process comprises the step of reacting a mixture comprising a mole ratio of ≥95% of a compound of Formula V as disclosed herein to ≤5% of a compound of Formula II as disclosed herein with hydrogen gas in the presence of a hydrogenation catalyst comprising rhodium and a chiral phosphine ligand (L') according to Formula VI as disclosed herein.

In some embodiments of the Formulas described herein, $R^5$ is selected from norbornyl, cyclohexyl, cyclopentyl, phenyl, and tert-butyl. In some embodiments, $R^5$ is norbornyl. In some embodiments, $R^5$ is cyclohexyl. In some embodiments, $R^5$ is phenyl. In some embodiments, $R^5$ is tert-butyl.

In some embodiments of the formulas described herein, each of $R^{2a}$, $R^{2b}$, $R^{3a}$, $R^{3b}$, and $R^4$ is hydrogen. In some embodiments, each of $R^{2a}$, $R^{2b}$, and $R^4$ is hydrogen, and $R^{3a}$ and $R^{3b}$ are each methyl or each trifluoromethyl. In some embodiments, each of $R^{2a}$ and $R^{2b}$ is hydrogen, $R^4$ is methoxy, and $R^{3a}$ and $R^{3b}$ are each methyl. In some embodiments, each of $R^{2a}$, $R^{2b}$, $R^{3a}$, and $R^{3b}$ is hydrogen, and $R^4$ is methoxy, trifluoromethyl, or methyl. In some embodiments, each of $R^{3a}$, $R^{3b}$, and $R^4$ is hydrogen, one of $R^{2a}$ and $R^{2b}$ is hydrogen and the other of $R^{2a}$ and $R^{2b}$ is methyl. In some embodiments, each of $R^{2a}$, $R^{2b}$, $R^{3a}$, $R^{3b}$, and $R^4$ is hydrogen, and $R^5$ is selected from norbornyl, cyclohexyl, cyclopentyl, phenyl, and tert-butyl. In some embodiments, each of $R^{2a}$, $R^{2b}$, $R^{3a}$, $R^{3b}$, and $R^4$ is hydrogen, and $R^5$ is norbornyl. In some embodiments, each of $R^{2a}$, $R^{2b}$, $R^{3a}$, $R^{3b}$, and $R^4$ is hydrogen, and $R^5$ is cyclohexyl. In some embodiments, each of $R^{2a}$, $R^{2b}$, $R^{3a}$, $R^{3b}$, and $R^4$ is hydrogen, and $R^5$ is phenyl. In some embodiments, each of $R^{2a}$, $R^{2b}$, $R^{3a}$, $R^{3b}$, and $R^4$ is hydrogen, and $R^5$ is tert-butyl.

In some embodiments of the formulas described herein, the hydrogenation catalyst is formed by mixing a rhodium pre-catalyst of the formula $[Rh(L_1)(L_2)]^+NC^-$ with the chiral phosphine ligand (L) of Formula III, (L') of Formula VI, or (L") of Formula VIII; wherein $L_1$ and $L_2$ are the same or different, $L_1$ and $L_2$ are each independently a pair of monodentate ligands or a bidentate ligand, wherein the monodentate ligand is selected from an alkene ligand and a solvent ligand, wherein the bidentate ligand is a diene; and wherein $NC^-$ is a non-coordinating counterion selected from tetrafluoroborate, triflate, hexafluorophosphate, hexafluoroantimonate, and perchlorate. In some embodiments, the alkene ligand may have one, two, three, four, or more double bonds. In some embodiments, the alkene ligand is selected from ethylene, cyclooctene, and norbornene. In some embodiments, the solvent ligand is selected from acetonitrile, tetrahydrofuran, 2-methyltetrahydrofuran, methanol, ethanol, trifluoroethanol, and isopropanol. In some embodiments, the diene ligand is selected from 1,5-cyclooctadiene (COD), 1,5-hexadiene, and norbornadiene. In some embodiments, the rhodium pre-catalyst is $[Rh(COD)_2]^+BF_4^-$.

In some embodiments, the hydrogenation catalyst comprises $[Rh(L_1)(L)]^+BF_4^-$, wherein $(L_1)$ is a pair of monodentate ligands or a bidentate ligand, and (L) is:

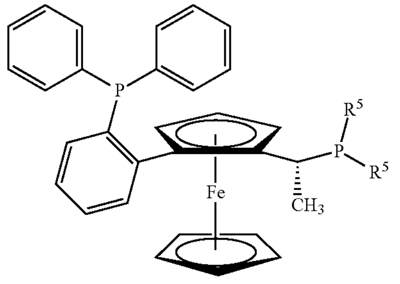

(1S)-1-[(1R)-1-(Dicyclohexylphosphino)ethyl]-2-[2-(diphenylphosphino)phenyl]ferrocene (CAS #565184-29-4), wherein $R^5$ is cyclohexyl. In some embodiments, the hydrogenation catalyst comprises $[Rh(COD)(565184-29-4)]^+BF_4^-$.

In some embodiments, the hydrogenation catalyst comprises $[Rh(L_1)(L')]^+BF_4^-$, wherein $(L_1)$ is a pair of monodentate ligands or a bidentate ligand, and (L') is:

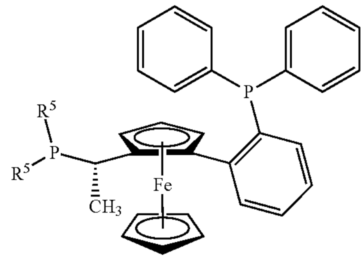

(1R)-1-[(1S)-1-(Dicyclohexylphosphino)ethyl]-2-[2-(diphenylphosphino)phenyl]ferrocene (CAS #849925-19-5), wherein $R^5$ is cyclohexyl. In some embodiments, the hydrogenation catalyst comprises $[Rh(COD)(849925-19-5)]^+BF_4^-$.

In some embodiments, the hydrogenation catalyst comprises $[Rh(L_1)(L)]^+BF_4^-$, wherein $(L_1)$ is a pair of monodentate ligands or a bidentate ligand, and (L) is:

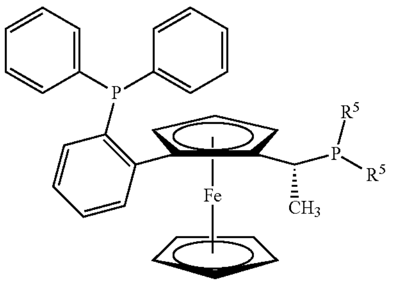

(1S)-1-[(1R)-1-[Bis(bicyclo[2.2.1]hept-2-yl)phosphino]ethyl]-2-[2-(diphenylphosphino)phenyl]ferrocene (CAS #849925-29-7), wherein $R^5$ is norbornyl. In some embodiments, the hydrogenation catalyst comprises $[Rh(COD)(849925-29-7)]^+BF_4^-$.

In some embodiments, the hydrogenation catalyst comprises $[Rh(L_1)(L')]^+BF_4^-$, wherein $(L_1)$ is a pair of monodentate ligands or a bidentate ligand, and (L') is:

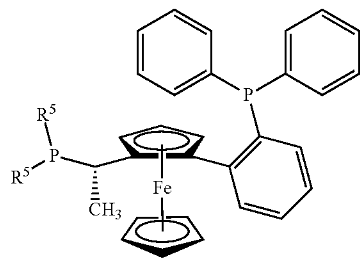

(1R)-1-[(1S)-1-[Bis(bicyclo[2.2.1]hept-2-yl)phosphino]ethyl]-2-[2-(diphenylphosphino)phenyl]ferrocene (CAS #849925-45-7), wherein $R^5$ is norbornyl. In some embodiments, the hydrogenation catalyst comprises $[Rh(COD)(849925-45-7)]^+BF_4^-$.

In some embodiments, the hydrogenation catalyst comprises $[Rh(L_1)(L')]^+BF_4^-$, wherein $(L_1)$ is a pair of monodentate ligands or a bidentate ligand, and (L') is:

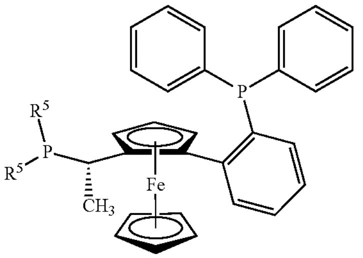

(S)-1-[(S)-1-(Diphenylphosphino)ethyl]-2-[2-(diphenylphosphino)phenyl]ferrocene (CAS #1854067-25-6), wherein $R^5$ is phenyl. In some embodiments, the hydrogenation catalyst comprises $[Rh(COD)(1854067\text{-}25\text{-}6)]^+BF_4^-$.

In some embodiments, the hydrogenation catalyst comprises $[Rh(L_1)(L'')]^+BF_4^-$, wherein ($L_1$) is a pair of monodentate ligands or a bidentate ligand, and (L") is:

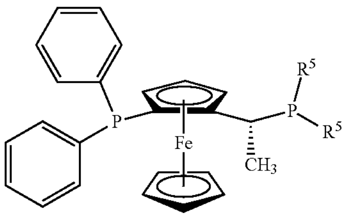

(R)-1-[(S)-2-(Diphenylphosphino)ferrocenyl]ethyldi-tert-butylphosphine (CAS #155830-69-6), wherein $R^5$ is tert-butyl. In some embodiments, the hydrogenation catalyst comprises $[Rh(COD)(155830\text{-}69\text{-}6)]^+BF_4^-$.

In some embodiments wherein $R^5$ is norbornyl, the norbornyl groups are bonded to the phosphorus atom in any of the following configurations shown in Table 1 below:

TABLE 1

| $Nb_1$ | | $Nb_2$ | | $P(Nb_1)(Nb_2)$ |
|---|---|---|---|---|
| endo | R | endo | R | N/A |
| exo | R | exo | R | N/A |
| endo | S | endo | S | N/A |
| exo | S | exo | S | N/A |
| endo | R | exo | R | $R_p$ |
| endo | R | endo | S | $R_p$ |
| endo | R | exo | S | $R_p$ |
| endo | R | exo | R | $S_p$ |
| endo | R | endo | S | $S_p$ |
| endo | R | exo | S | $S_p$ |
| exo | R | endo | R | $R_p$ |
| exo | R | endo | S | $R_p$ |
| exo | R | exo | S | $R_p$ |
| exo | R | endo | R | $S_p$ |
| exo | R | endo | S | $S_p$ |
| exo | R | exo | S | $S_p$ |
| endo | S | exo | S | $R_p$ |
| endo | S | endo | R | $R_p$ |
| endo | S | exo | R | $R_p$ |
| endo | S | exo | S | $S_p$ |
| endo | S | endo | R | $S_p$ |
| endo | S | exo | R | $S_p$ |
| exo | S | endo | S | $R_p$ |
| exo | S | endo | R | $R_p$ |
| exo | S | exo | R | $R_p$ |
| exo | S | endo | S | $S_p$ |
| exo | S | endo | R | $S_p$ |
| exo | S | exo | R | $S_p$ |

wherein (1S)-exo-norbornyl is

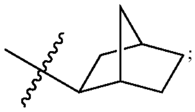 [SMILES: *C1CC2CCC1C2]
;

(1R)-exo-norbornyl is

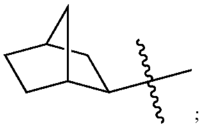 [SMILES: *C1CC2CCC1C2]
;

(1S)-endo-norbornyl is

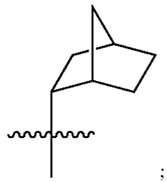 [SMILES: *C1CC2CCC1C2]
;

and (1R)-endo-norbornyl is

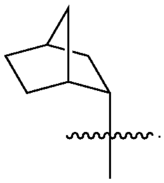 [SMILES: *C1CC2CCC1C2]
.

In some embodiments, the chiral phosphine ligand (L) according to Formula III or (L') according to Formula VI, wherein $R^5$ is norbornyl, comprises a single isomer selected from Table 1, or comprises a mixture of 2, 3, 4, or more isomers selected from Table 1. The column $P(Nb_1)(Nb_2)$ provides the stereochemical configuration of the phosphorus atom.

In some embodiments, the step of reacting is performed in a solvent. Non-limiting examples of the solvent include dichloromethane, tetrahydrofuran, 2-methyltetrahydrofuran, methanol, ethanol, trifluoroethanol, isopropanol, ethyl acetate, isopropyl acetate, and mixtures thereof. In some embodiments, the solvent is dichloromethane. In some embodiments, the solvent is tetrahydrofuran. In some embodiments, the solvent is trifluoroethanol.

In some embodiments, hydrogen gas is present in the reaction step at a pressure of 20 bar or less. In some embodiments, hydrogen gas is present at a pressure of 15 bar or less. In some embodiments, hydrogen gas is present at a pressure of 10 bar or less. In some embodiments, hydrogen gas is present at a pressure of 5 bar or less.

After testing numerous catalysts comprising various metal and chiral ligand combinations known for use in asymmetric hydrogenation of acrylonitriles, all of which failed to provide high enantiomeric excess of and/or high conversion to the (R)-enantiomer of a compound of Formula I, the inventors have unexpectedly found that the hydrogenation catalysts disclosed herein do provide high enantiomeric excess of and conversion to the (R)-enantiomer of a compound of Formula I. In some embodiments, the process forms a compound of Formula I having an enantiomeric excess of the (R)-enantiomer of at least 70%. In some embodiments, the process forms a compound of Formula I having an enantiomeric excess of the (R)-enantiomer of at least 80%. In some embodiments, the process forms a compound of Formula I having an enantiomeric excess of the (R)-enantiomer of at least 90%. In some embodiments, the process forms a compound of Formula I having an enantiomeric excess of the (R)-enantiomer of at least 95%. In some embodiments, the process forms a compound of Formula I having an enantiomeric excess of the (R)-enantiomer of at least 97%. In some embodiments, the process forms a compound of Formula I having an enantiomeric excess of the (R)-enantiomer of at least 98%. In some embodiments, the process forms a compound of Formula I having an enantiomeric excess of the (R)-enantiomer of at least 99%.

For asymmetric hydrogenations described herein which produce a low enantiomeric excess of the (R)-enantiomer of a compound of Formula I, the inventors have discovered a method to crystallize the compound of Formula I to upgrade the enantiomeric excess. After testing over twenty protecting groups (PG), the inventors have unexpectedly found that only when PG is tosyl can the compound of Formula I be crystallized to increase the enantiomeric excess.

Accordingly, certain aspects of the present invention are directed to processes for increasing the enantiomeric excess of a compound of Formula I, comprising the steps of:

providing a compound of Formula I:

Formula I

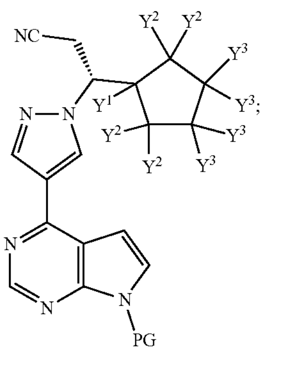

wherein $Y^1$ is hydrogen or deuterium, each $Y^2$ is the same and is hydrogen or deuterium, each $Y^3$ is the same and is hydrogen or deuterium, PG is tosyl (Ts), and having a starting enantiomeric excess of the (R)-enantiomer of at least 70%; dissolving the compound in aqueous ethanol, and crystallizing the compound to provide a final enantiomeric excess of the (R)-enantiomer of at least 98%.

In some embodiments of the formulas described herein, each of $Y^1$, $Y^2$, and $Y^3$ is hydrogen. In some embodiments, each of $Y^1$, $Y^2$, and $Y^3$ is deuterium. In some embodiments, $Y^1$ is hydrogen and each of $Y^2$ and $Y^3$ is deuterium. In some embodiments, each of $Y^1$ and $Y^2$ is hydrogen and each of $Y^3$ is deuterium. In some embodiments, each of $Y^1$ and $Y^3$ is hydrogen and each of $Y^2$ is deuterium. In some embodiments, $Y^1$ is at least 95% hydrogen. In some embodiments, $Y^1$ is at least 96% hydrogen. In some embodiments, $Y^1$ is at least 97% hydrogen. In some embodiments, $Y^1$ is at least 98% hydrogen. In some embodiments, $Y^1$ is at least 99% hydrogen.

In some embodiments, the aqueous ethanol is 80%, 90%, or 95% ethanol by volume (v/v). In some embodiments, the aqueous ethanol is 95% ethanol.

In some embodiments, the step of crystallizing comprises forming a hemihydrate of the compound of Formula I. In some embodiments, the step of crystallizing comprises heating the compound of Formula I dissolved in aqueous ethanol to about 50° C. until a solid hemihydrate forms, and then cooling the solution to about 20° C. As used herein, the term "hemihydrate" includes 0.3-0.7 moles of water per mole of compound of Formula I, 0.4-0.6 moles of water per mole of compound of Formula I, or about 0.5 moles of water per mole of compound of Formula I.

In some embodiments, starting enantiomeric excess of the (R)-enantiomer of the compound of Formula I is at least 70%, and the final enantiomeric excess is at least 98%. In some embodiments, the starting enantiomeric excess is at least 86% and the final enantiomeric excess is at least 98.8%. In some embodiments, the starting enantiomeric excess is at least 94% and the final enantiomeric excess is at least 99%. In some embodiments, the starting enantiomeric excess is at least 96% and the final enantiomeric excess is at least 99%.

In some embodiments, the process further comprises the step of removing the tosyl group. In some embodiments, the tosyl group is removed by treating with base, including but not limited to, cesium carbonate or potassium hydroxide. In some embodiments, the tosyl group is removed by treating with potassium hydroxide.

In some embodiments, the process further comprises the step of forming a pharmaceutically acceptable salt of the compound of Formula I. In some embodiments, a phosphoric acid salt of the compound of Formula I is formed by treating with phosphoric acid.

Intermediates

Certain aspects of the present invention are directed to intermediates useful, e.g., in the preparation of compounds of Formula I. In some embodiments, the intermediate comprises a compound of Formula II:

Formula II

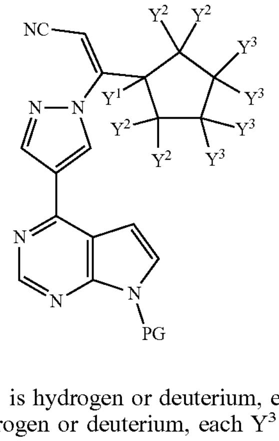

wherein $Y^1$ is hydrogen or deuterium, each $Y^2$ is the same and is hydrogen or deuterium, each $Y^3$ is the same and is hydrogen or deuterium; and PG is hydrogen or a protecting group selected from pivaloyloxymethyl (POM), 2-(trimethylsilyl)ethoxymethyl (SEM), benzyl (Bn), p-methoxybenzyl (PMB), 3,4-dimethoxybenzyl (DMPM), 2,4-dimethoxybenzyl, benzenesulfonyl, tosyl (Ts), t-butoxycarbonyl (BOC), methoxycarbonyl (MOC), benzyloxycarbonyl (CBz), 1-naphthalenesulfonate (1-napsyl), 4-nitrobenzenesulfonyl (p-nosyl), and 2,4,6-trimethylphenylsulfonyl.

In some embodiments, the intermediate comprises a compound of Formula V:

Formula V

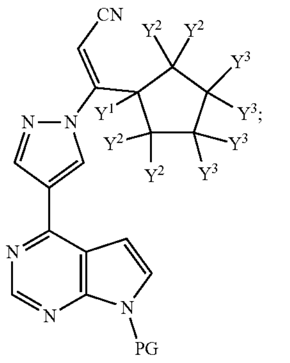

wherein $Y^1$ is hydrogen or deuterium, each $Y^2$ is the same and is hydrogen or deuterium, each $Y^3$ is the same and is hydrogen or deuterium; and PG is hydrogen or a protecting group selected from pivaloyloxymethyl (POM), 2-(trimethylsilyl)ethoxymethyl (SEM), benzyl (Bn), p-methoxybenzyl (PMB), 3,4-dimethoxybenzyl (DMPM), 2,4-dimethoxybenzyl, benzenesulfonyl, tosyl (Ts), t-butoxycarbonyl (BOC), methoxycarbonyl (MOC), benzyloxycarbonyl (CBz), 1-naphthalenesulfonate (1-napsyl), 4-nitrobenzenesulfonyl (p-nosyl), and 2,4,6-trimethylphenylsulfonyl.

In some embodiments, the intermediate comprises a compound of Formula VII:

Formula VII

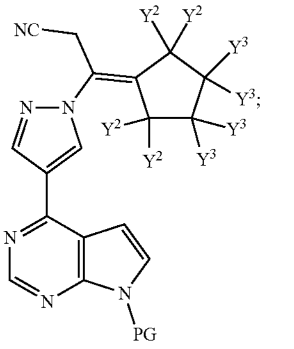

wherein each $Y^2$ is the same and is hydrogen or deuterium, each $Y^3$ is the same and is hydrogen or deuterium, provided that at least one of $Y^2$ and $Y^3$ is deuterium; and PG is hydrogen or a protecting group selected from pivaloyloxymethyl (POM), 2-(trimethylsilyl)ethoxymethyl (SEM), benzyl (Bn), p-methoxybenzyl (PMB), 3,4-dimethoxybenzyl (DMPM), 2,4-dimethoxybenzyl, benzenesulfonyl, tosyl (Ts), t-butoxycarbonyl (BOC), methoxycarbonyl (MOC), benzyloxycarbonyl (CBz), 1-naphthalenesulfonate (1-napsyl), 4-nitrobenzenesulfonyl (p-nosyl), and 2,4,6-trimethylphenylsulfonyl.

In some embodiments of the formulas described herein, PG is tosyl (Ts). In some embodiments, PG is pivaloyloxymethyl (POM). In some embodiments, PG is 2-(trimethylsilyl) ethoxymethyl (SEM). In some embodiments, PG is hydrogen.

In some embodiments of the formulas described herein, each of $Y^1$, $Y^2$, and $Y^3$ is hydrogen. In some embodiments, each of $Y^1$, $Y^2$, and $Y^3$ is deuterium. In some embodiments, $Y^1$ is hydrogen and each of $Y^2$ and $Y^3$ is deuterium. In some embodiments, each of $Y^1$ and $Y^2$ is hydrogen and each of $Y^3$ is deuterium. In some embodiments, each of $Y^1$ and $Y^3$ is hydrogen and each of $Y^2$ is deuterium. In some embodiments, $Y^1$ is at least 95% hydrogen. In some embodiments, $Y^1$ is at least 96% hydrogen. In some embodiments, $Y^1$ is at least 97% hydrogen. In some embodiments, $Y^1$ is at least 98% hydrogen. In some embodiments, $Y^1$ is at least 99% hydrogen.

In some embodiments of Formula VII, each of $Y^2$ and $Y^3$ is deuterium. In some embodiments, each of $Y^2$ is deuterium and each of $Y^3$ is hydrogen. In some embodiments, each of $Y^2$ is hydrogen and each of $Y^3$ is deuterium.

In some embodiments of the formulas described herein, when $Y^1$ is deuterium, the level of deuterium incorporation at $Y^1$ is at least 52.5%, at least 75%, at least 82.5%, at least 90%, at least 95%, is at least 97%, or at least 99%. In some embodiments when $Y^1$ is hydrogen, the level of deuterium incorporation at $Y^1$ is about 1-2%. In some embodiments when $Y^1$ is hydrogen, the level of deuterium incorporation at $Y^1$ is at the natural isotopic abundance of deuterium.

In some embodiments of the formulas described herein, when $Y^2$ is deuterium, the level of deuterium incorporation at each $Y^2$ is at least 52.5%, at least 75%, at least 82.5%, at least 90%, at least 95%, is at least 97%, or at least 99%.

In some embodiments of the formulas described herein, when $Y^3$ is deuterium, the level of deuterium incorporation at each $Y^3$ is at least 52.5%, at least 75%, at least 82.5%, at least 90%, at least 95%, is at least 97%, or at least 99%.

In another set of embodiments of the formulas described herein, any atom not designated as deuterium in any of the embodiments set forth herein is present at its natural isotopic abundance.

In some embodiments of the formulas described herein, deuterium incorporation at each designated deuterium atom is at least 52.5%, at least 75%, at least 82.5%, at least 90%, at least 95%, at least 97%, or at least 99%.

In some embodiments of the formulas described herein, at least one of $Y^1$, $Y^2$, and $Y^3$ is hydrogen.

The synthesis of compounds of Formula II, Formula V, or Formula VII may be readily achieved by synthetic chemists of ordinary skill by reference to the Exemplary Synthesis disclosed herein. Relevant procedures analogous to those of use for the preparation of compounds of Formula II, Formula V, Formula VII and intermediates thereof are disclosed, for example, in U.S. Pat. No. 8,410,265.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

Compounds of Formula II, Formula V, or Formula VII may be prepared in a manner analogous to those syntheses presented in U.S. Pat. No. 8,410,265 using appropriately deuterated starting materials.

A convenient method for synthesizing compounds of Formula II, Formula V, or Formula VII is depicted in the Schemes below.

Scheme 1
Preparation of a Compound of Formula II

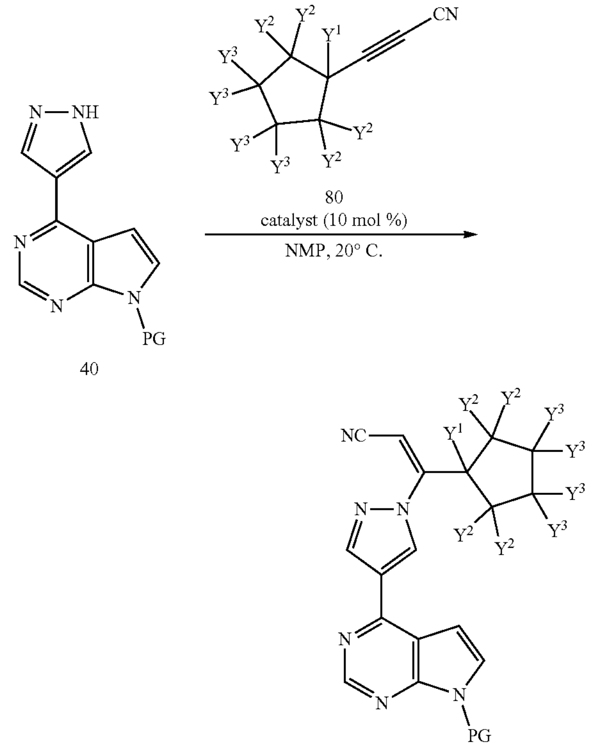

40 80 20

Scheme 1 discloses an exemplary synthesis of a compound of Formula II.

Compound 40 is treated with a nucleophilic catalyst (10 mol %) and compound 80 in N-Methyl-2-pyrrolidone (NMP) at room temperature to afford compound 20. Examples of nucleophilic catalysts include, but are not limited to, tetrabutylammonium halides (e.g., $nBu_4NI$, $nBu_4NBr$, etc.), soluble iodides (e.g., butylmethylimidazolium iodide, etc.), inorganic iodides (e.g., potassium iodide, etc.), azabicyclo[2.2.2] catalysts (e.g.,  , etc.), 4-aminopyridine catalysts (e.g., 4-dimethylaminopyridine,

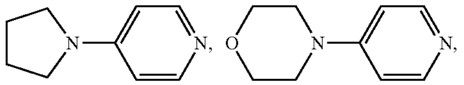

etc.), and phosphine catalysts (e.g., tributylphosphine, etc.). Compound 40 may be prepared in a manner analogous to those described in U.S. Pat. Nos. 9,249,149 and 8,410,265, using appropriately deuterated starting materials if desired. Compound 80 may be prepared according to Scheme 2 below.

Scheme 2
Preparation of a Compound 80

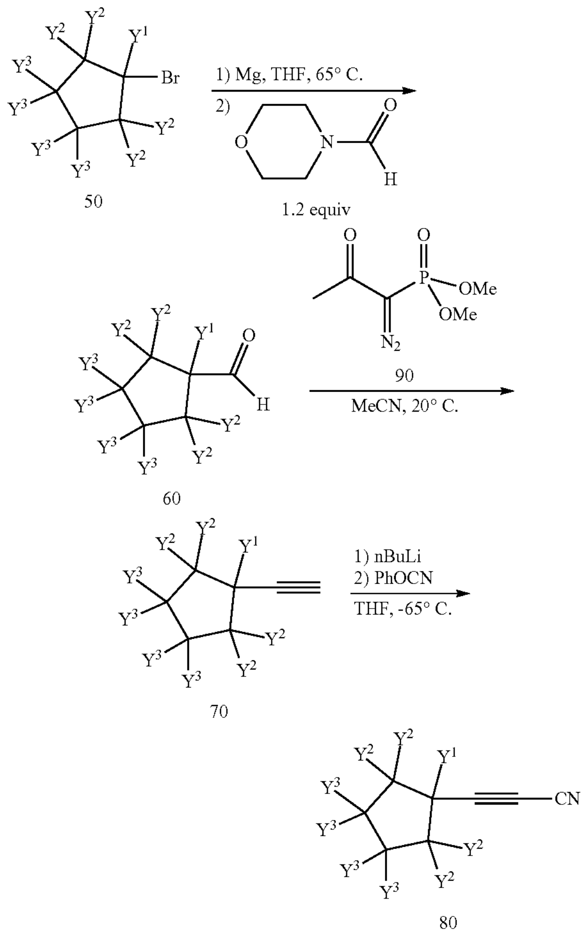

50 60 70 80

Appropriately deuterated compound 50 is treated with magnesium metal in tetrahydrofuran (THF) at elevated temperature to afford the corresponding Grignard reagent, to which excess N-formyl morpholine is added. Acidic workup affords compound 60. For example, compound 50 wherein each of $Y^1$, $Y^2$, and $Y^3$ is deuterium is commercially available. Alternatively, compound 60 wherein each $Y^1$ and $Y^3$ is hydrogen and each $Y^2$ is deuterium may be prepared according to Example 1 (compound 35) of U.S. Pat. No. 9,249,149. Alternatively, compound 60 wherein each $Y^1$ and $Y^2$ is hydrogen and each $Y^3$ is deuterium may be prepared according to Example 2 (compound 43) of U.S. Pat. No. 9,249,149.

Then, a solution of appropriately deuterated compound 60 in MeOH is added to dimethyl (1-diazo-2-oxopropyl)phosphonate 90 in acetonitrile and the reaction mixture is stirred at room temperature. Work up and purification affords compound 70. Dimethyl (1-diazo-2-oxopropyl)phosphonate 90 is provided by adding dimethyl-2-oxopropylphosphonate to a reaction vessel charged with potassium carbonate and tosyl azide in acetonitrile.

Compound 70 is first treated with n-butyllithium in THF at reduced temperature, and then phenylcyanate in THF is added to the reaction mixture. Work up and purification affords compound 80. Phenylcyanate is provided by treating phenol and cyanogen bromide in hexane and ethyl ether with triethylamine at 0° C., and then filtering to produce phenyl cyanate.

Use of appropriately deuterated reagents allows deuterium incorporation at the $Y^1$, $Y^2$, and $Y^3$ positions of a compound of Formula I, Formula II, or Formula V or any appropriate intermediate herein, e.g., about 90%, about 95%, about 97%, about 98%, or about 99% deuterium incorporation at any of $Y^1$, $Y^2$, and/or $Y^3$.

Scheme 3

Preparation of a Compound of Formula V

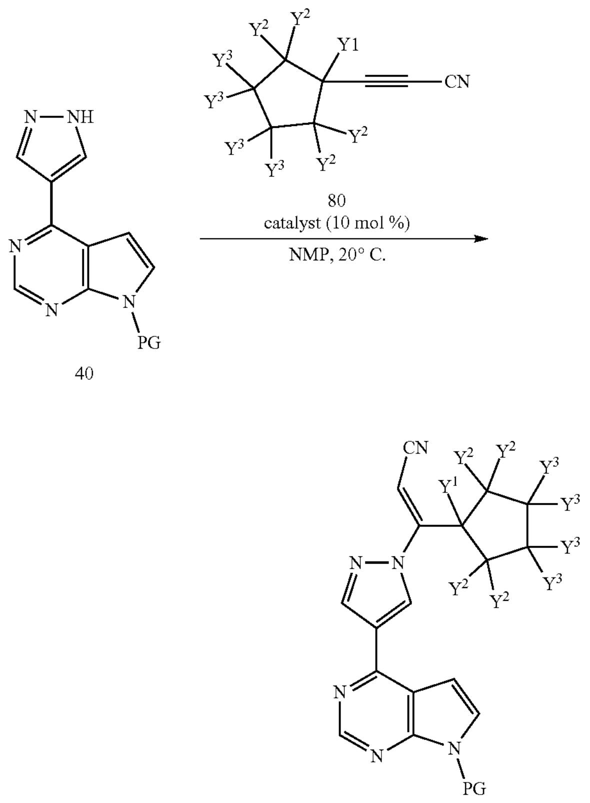

40

80

30

Scheme 3 discloses an exemplary synthesis of a compound of Formula V. Compound 40 is treated with a nucleophilic catalyst (10 mol %) and compound 80 in N-Methyl-2-pyrrolidone (NMP) at room temperature to afford compound 30. In some embodiments, the nucleophilic catalyst is quinuclidine.

Scheme 4

Preparation of a Compound of Formula VII

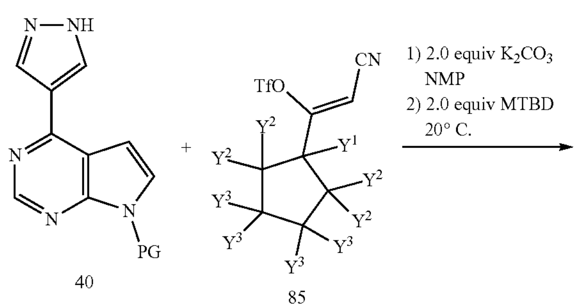

40

+

85

-continued

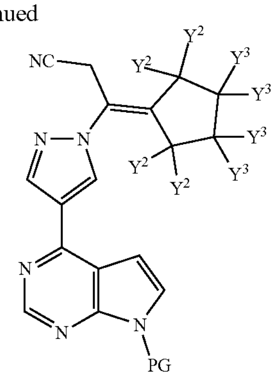

95

Scheme 4 discloses an exemplary synthesis of a compound of Formula VII. Compound 40 is treated with a base, such as potassium carbonate, and enol triflate 85 in N-Methyl-2-pyrrolidone (NMP) at 20° C. to afford compound 95. Enol triflate 85 may be prepared according to procedures disclosed in International Application No. PCT/US20/17093.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $Y^1$, Y, $Y^3$, etc.) or not. The suitability of a chemical group in a compound structure for use in the synthesis of another compound is within the knowledge of one of ordinary skill in the art.

Additional methods of synthesizing compounds of Formula I, II, and V and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, 3rd Ed., John Wiley and Sons (1999); Fieser, L et al., *Fieser and Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Reaction Mixtures

Certain aspects of the present invention are directed to reaction mixtures. In some embodiments, the reaction mixture comprises:

(a) a compound of Formula II:

Formula II

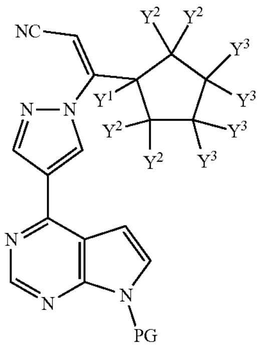

wherein $Y^1$ is hydrogen or deuterium, each $Y^2$ is the same and is hydrogen or deuterium, each $Y^3$ is the same and is hydrogen or deuterium; and PG is hydrogen or a protecting group selected from pivaloyloxymethyl (POM), 2-(trimethylsilyl)ethoxymethyl (SEM), benzyl (Bn), p-methoxybenzyl (PMB), 3,4-dimethoxybenzyl (DMPM), 2,4-dimethoxybenzyl, benzenesulfonyl, tosyl (Ts), t-butoxycarbonyl (BOC), methoxycarbonyl (MOC), benzyloxycarbonyl (CBz), 1-naphthalenesulfonate (1-napsyl), 4-nitrobenzenesulfonyl (p-nosyl), and 2,4,6-trimethylphenylsulfonyl;

(b) a hydrogenation catalyst comprising rhodium and a chiral phosphine ligand (L) according to Formula III:

Formula III

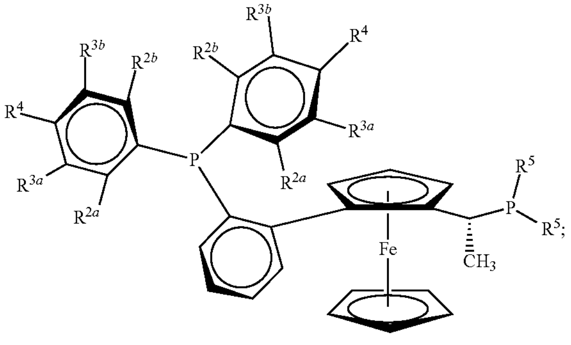

wherein each of $R^{2a}$, $R^{2b}$, $R^{3a}$, $R^{3b}$, and $R^4$ is independently selected from hydrogen, methyl, methoxy, and trifluoromethyl; and $R^5$ is secondary alkyl, tertiary alkyl, or cycloalkyl; and (c) a solvent selected from dichloromethane, tetrahydrofuran, 2-methyltetrahydrofuran, methanol, ethanol, trifluoroethanol, isopropanol, ethyl acetate, isopropyl acetate and mixtures thereof.

In some embodiments, the reaction mixture comprises:

(a) a compound of Formula V:

Formula V

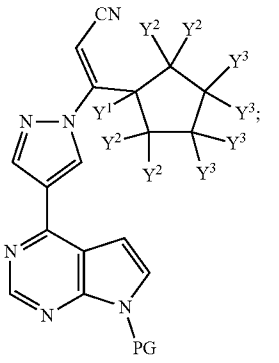

wherein $Y^1$ is hydrogen or deuterium, each $Y^2$ is the same and is hydrogen or deuterium, each $Y^3$ is the same and is hydrogen or deuterium; and PG is hydrogen or a protecting group selected from pivaloyloxymethyl (POM), 2-(trimethylsilyl)ethoxymethyl (SEM), benzyl (Bn), p-methoxybenzyl (PMB), 3,4-dimethoxybenzyl (DMPM), 2,4-dimethoxybenzyl, benzenesulfonyl, tosyl (Ts), t-butoxycarbonyl (BOC), methoxycarbonyl (MOC), benzyloxycarbonyl (CBz), 1-naphthalenesulfonate (1-napsyl), 4-nitrobenzenesulfonyl (p-nosyl), and 2,4,6-trimethylphenylsulfonyl;

(b) a hydrogenation catalyst comprising rhodium and a chiral phosphine ligand (L') according to Formula VI:

Formula VI

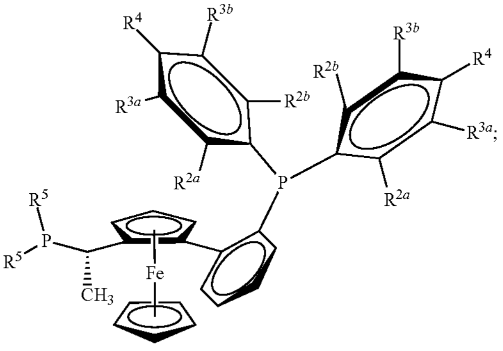

wherein each of $R^{2a}$, $R^{2b}$, $R^{3a}$, $R^{3b}$, and $R^4$ is independently selected from hydrogen, methyl, methoxy, and trifluoromethyl; and $R^5$ is secondary alkyl, tertiary alkyl, or cycloalkyl; and (c) a solvent selected from dichloromethane, tetrahydrofuran, 2-methyltetrahydrofuran, methanol, ethanol, trifluoroethanol, isopropanol, ethyl acetate, isopropyl acetate, and mixtures thereof.

In some embodiments, the reaction mixture comprises:

a. a compound of Formula VII:

Formula VII

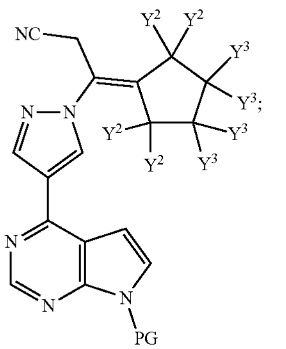

wherein each $Y^2$ is the same and is hydrogen or deuterium, each $Y^3$ is the same and is hydrogen or deuterium; and PG is hydrogen or a protecting group selected from pivaloyloxymethyl (POM), 2-(trimethylsilyl)ethoxymethyl (SEM), benzyl (Bn), p-methoxybenzyl (PMB), 3,4-dimethoxybenzyl (DMPM), 2,4-dimethoxybenzyl, benzenesulfonyl, tosyl (Ts), t-butoxycarbonyl (BOC), methoxycarbonyl (MOC), benzyloxycarbonyl (CBz), 1-naphthalenesulfonate (1-napsyl), 4-nitrobenzenesulfonyl (p-nosyl), and 2,4,6-trimethylphenylsulfonyl;

b. a hydrogenation catalyst comprising rhodium and a chiral phosphine ligand (L') according to Formula VI or (L") according to Formula VIII:

Formula VI

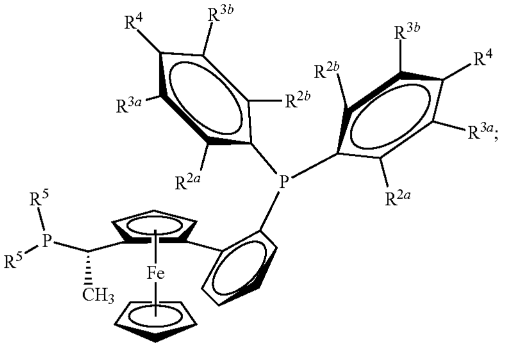

wherein each of $R^{2a}$, $R^{2b}$, $R^{3a}$, $R^{3b}$, and $R^4$ is independently selected from hydrogen, methyl, methoxy, and trifluoromethyl; and $R^5$ is phenyl; or Formula VIII

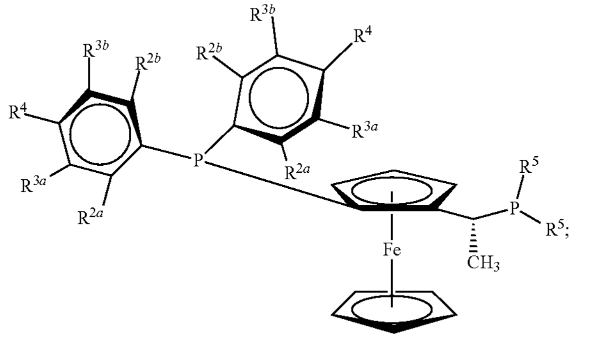

wherein each of $R^{2a}$, $R^{2b}$, $R^{3a}$, $R^{3b}$, and $R^4$ is independently selected from hydrogen, methyl, methoxy, and trifluoromethyl; and $R^5$ is tert-butyl; and c. a solvent selected from dichloromethane, tetrahydrofuran, 2-methyltetrahydrofuran, methanol, ethanol, trifluoroethanol, isopropanol, ethyl acetate, isopropyl acetate, and mixtures thereof.

In some embodiments, the solvent is dichloromethane. In some embodiments, the solvent is tetrahydrofuran. In some embodiments, the solvent is trifluoroethanol.

In some embodiments of the formulas described herein, PG is tosyl. In some embodiments, PG is pivaloyloxymethyl (POM). In some embodiments, PG is 2-(trimethylsilyl)ethoxymethyl (SEM). In some embodiments, PG is hydrogen.

In some embodiments of the formulas described herein, each of $Y^1$, $Y^2$, and $Y^3$ is hydrogen. In some embodiments, each of $Y^1$, $Y^2$, and $Y^3$ is deuterium. In some embodiments, $Y^1$ is hydrogen and each of $Y^2$ and $Y^3$ is deuterium. In some embodiments, each of $Y^1$ and $Y^2$ is hydrogen and each of $Y^3$ is deuterium. In some embodiments, each of $Y^1$ and $Y^3$ is hydrogen and each of $Y^2$ is deuterium. In some embodiments, $Y^1$ is at least 95% hydrogen. In some embodiments, $Y^1$ is at least 96% hydrogen. In some embodiments, $Y^1$ is at least 97% hydrogen. In some embodiments, $Y^1$ is at least 98% hydrogen. In some embodiments, $Y^1$ is at least 99% hydrogen.

In some embodiments, the reaction mixture comprises a mole ratio of ≥80% of a compound of Formula II as disclosed herein to ≤20% of a compound of Formula V as disclosed herein, and a hydrogenation catalyst comprising rhodium and a chiral phosphine ligand (L) according to Formula III as disclosed herein. In some embodiments, the reaction mixture comprises a mole ratio of ≥90% of a compound of Formula II as disclosed herein to ≤10% of a compound of Formula V as disclosed herein, and a hydrogenation catalyst comprising rhodium and a chiral phosphine ligand (L) according to Formula III as disclosed herein. In some embodiments, the reaction mixture comprises a mole ratio of ≥95% of a compound of Formula II as disclosed herein to ≤5% of a compound of Formula V as disclosed herein, and a hydrogenation catalyst comprising rhodium and a chiral phosphine ligand (L) according to Formula III as disclosed herein.

In some embodiments, the reaction mixture comprises a mole ratio of ≥80% of a compound of Formula V as disclosed herein to ≤20% of a compound of Formula II as disclosed herein, and a hydrogenation catalyst comprising rhodium and a chiral phosphine ligand (L') according to Formula VI as disclosed herein. In some embodiments, the reaction mixture comprises a mole ratio of ≥90% of a compound of Formula V as disclosed herein to ≤10% of a compound of Formula II as disclosed herein with hydrogen gas in the presence of a hydrogenation catalyst comprising rhodium and a chiral phosphine ligand (L') according to Formula VI as disclosed herein. In some embodiments, the reaction mixture comprises a mole ratio of ≥95% of a compound of Formula V as disclosed herein to ≤5% of a compound of Formula II as disclosed herein with hydrogen gas in the presence of a hydrogenation catalyst comprising rhodium and a chiral phosphine ligand (L') according to Formula VI as disclosed herein.

In some embodiments of the formulas described herein, $R^5$ is selected from norbornyl, cyclohexyl, cyclopentyl, and tert-butyl. In some embodiments, $R^5$ is norbornyl. In some embodiments, $R^5$ is cyclohexyl.

In some embodiments of the formulas described herein, each of $R^{2a}$, $R^{2b}$, $R^{3a}$, $R^{3b}$, and $R^4$ is hydrogen. In some embodiments, each of $R^{2a}$, $R^{2b}$, and $R^4$ is hydrogen, and $R^{3a}$ and $R^{3b}$ are each methyl or each trifluoromethyl. In some embodiments, each of $R^{2a}$ and $R^{2b}$ is hydrogen, $R^4$ is methoxy, and $R^{3a}$ and $R^{3b}$ are each methyl. In some embodiments, each of $R^{2a}$, $R^{2b}$, $R^{3a}$, and $R^{3b}$ is hydrogen, and $R^4$ is methoxy, trifluoromethyl, or methyl. In some embodiments, each of $R^{3a}$, $R^{3b}$, and $R^4$ is hydrogen, one of $R^{2a}$ and $R^{2b}$ is hydrogen and the other of $R^{2a}$ and $R^{2b}$ is methyl. In some embodiments, each of $R^{2a}$, $R^{2b}$, $R^{3a}$, $R^{3b}$, and $R^4$ is hydrogen, and $R^5$ is selected from norbornyl, cyclohexyl, cyclopentyl, and tert-butyl. In some embodiments, each of $R^{2a}$, $R^{2b}$, $R^{3a}$, $R^{3b}$, and $R^4$ is hydrogen, and $R^5$ is norbornyl. In some embodiments, each of $R^{2a}$, $R^{2b}$, $R^{3a}$, $R^{3b}$, and $R^4$ is hydrogen, and $R^5$ is cyclohexyl.

In some embodiments, the hydrogenation catalyst comprises $[Rh(L_1)(L)]^+NC^-$ or $[Rh(L_1)(L')]^+NC$, wherein $L_1$ is a pair of monodentate ligands or a bidentate ligand, wherein the monodentate ligand is selected from an alkene ligand and a solvent ligand, wherein the bidentate ligand is a diene, wherein L is a chiral phosphine ligand of Formula III, wherein L' is a chiral phosphine ligand of Formula VI, and wherein $NC^-$ is a non-coordinating counterion selected from tetrafluoroborate, triflate, hexafluorophosphate, hexafluoroantimonate, and perchlorate. In some embodiments, the alkene ligand is selected from 1,5-cyclooctadiene (COD), cyclooctene, 1,5-hexadiene and norbornadiene. In some embodiments, the alkene ligand may have one, two, three, four, or more double bonds. In some embodiments, the solvent ligand is selected from acetonitrile, tetrahydrofuran, 2-methyltetrahydrofuran, methanol, ethanol, trifluoroethanol, and isopropanol. In some embodiments, the diene ligand is selected from 1,5-cyclooctadiene (COD), 1,5-hexadiene, and norbornadiene. In some embodiments, the hydrogenation catalyst comprises $[Rh(COD)(L)]^+BF_4^-$. In some embodiments, the hydrogenation catalyst comprises $[Rh(COD)(L')]^+BF_4^-$.

In some embodiments, the hydrogenation catalyst comprises $[Rh(L_1)(L)]^+BF_4^-$, wherein $(L_1)$ is a pair of monodentate ligands or a bidentate ligand, and (L) is:

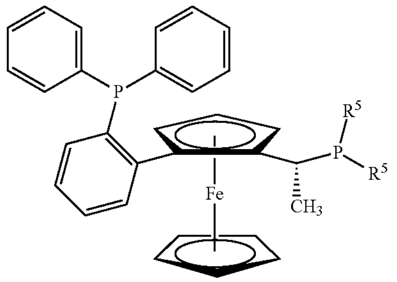

(1S)-1-[(1R)-1-(Dicyclohexylphosphino)ethyl]-2-[2-(diphenylphosphino)phenyl]ferrocene (CAS #565184-29-4), wherein $R^5$ is cyclohexyl. In some embodiments, the hydrogenation catalyst comprises $[Rh(COD)(565184\text{-}29\text{-}4)]^+BF_4^-$.

In some embodiments, the hydrogenation catalyst comprises $[Rh(L_1)(L')]^+BF_4^-$, wherein $(L_1)$ is a pair of monodentate ligands or a bidentate ligand, and (L') is:

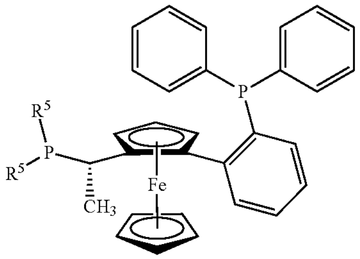

(1R)-1-[(1S)-1-(Dicyclohexylphosphino)ethyl]-2-[2-(diphenylphosphino)phenyl]ferrocene (CAS #849925-19-5), wherein $R^5$ is cyclohexyl. In some embodiments, the hydrogenation catalyst comprises $[Rh(COD)(849925\text{-}19\text{-}5)]^+BF_4^-$.

In some embodiments, the hydrogenation catalyst comprises $[Rh(L_1)(L)]^+BF_4^-$, wherein $(L_1)$ is a pair of monodentate ligands or a bidentate ligand, and (L) is:

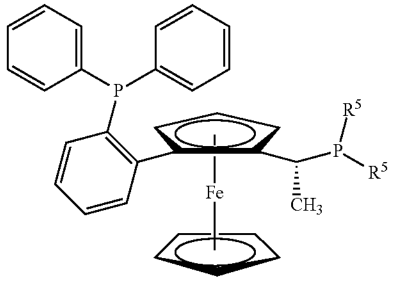

(1S)-1-[(1R)-1-[Bis(bicyclo[2.2.1]hept-2-yl)phosphino]ethyl]-2-[2-(diphenylphosphino)phenyl]ferrocene (CAS #849925-29-7), wherein $R^5$ is norbornyl. In some embodiments, the hydrogenation catalyst comprises $[Rh(COD)(849925\text{-}29\text{-}7)]^+BF_4^-$.

In some embodiments, the hydrogenation catalyst comprises $[Rh(L_1)(L')]^+BF_4^-$, wherein $(L_1)$ is a pair of monodentate ligands or a bidentate ligand, and (L') is:

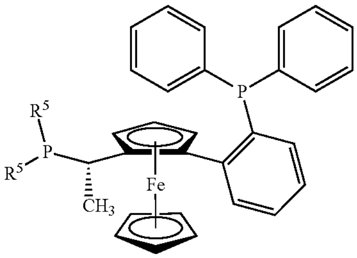

(1R)-1-[(1S)-1-[Bis(bicyclo[2.2.1]hept-2-yl)phosphino]ethyl]-2-[2-(diphenylphosphino)phenyl]ferrocene (CAS #849925-45-7), wherein $R^5$ is norbornyl. In some embodiments, the hydrogenation catalyst comprises $[Rh(COD)(849925\text{-}45\text{-}7)]^+BF_4$.

In some embodiments, the hydrogenation catalyst comprises $[Rh(L_1)(L')]^+BF_4^-$, wherein ($L_1$) is a pair of monodentate ligands or a bidentate ligand, and (L') is:

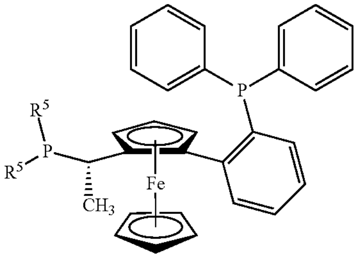

(S)-1-[(S)-1-(Diphenylphosphino)ethyl]-2-[2-(diphenylphosphino)phenyl]ferrocene (CAS #1854067-25-6), wherein $R^5$ is phenyl. In some embodiments, the hydrogenation catalyst comprises $[Rh(COD)(1854067\text{-}25\text{-}6)]^+BF_4^-$.

In some embodiments, the hydrogenation catalyst comprises $[Rh(L_1)(L'')]^+BF_4^-$, wherein ($L_1$) is a pair of monodentate ligands or a bidentate ligand, and (L") is:

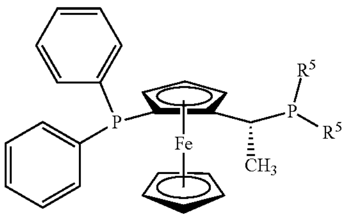

(R)-1-[(S)-2-(Diphenylphosphino)ferrocenyl]ethyldi-tert-butylphosphine (CAS #155830-69-6), wherein $R^5$ is tert-butyl. In some embodiments, the hydrogenation catalyst comprises $[Rh(COD)(155830\text{-}69\text{-}6)]^+BF_4^-$.

In some embodiments of the formulas described herein wherein $R^5$ is norbornyl, the norbornyl groups are bonded to the phosphorus atom in any of the following configurations shown in Table 1 below:

TABLE 1

| $Nb_1$ | | $Nb_2$ | | $P(Nb_1)(Nb_2)$ |
|---|---|---|---|---|
| endo | R | endo | R | N/A |
| exo | R | exo | R | N/A |
| endo | S | endo | S | N/A |
| exo | S | exo | S | N/A |
| endo | R | exo | R | $R_p$ |
| endo | R | endo | S | $R_p$ |
| endo | R | exo | S | $R_p$ |
| endo | R | exo | R | $S_p$ |
| endo | R | endo | S | $S_p$ |
| endo | R | exo | S | $S_p$ |
| exo | R | endo | R | $R_p$ |
| exo | R | endo | S | $R_p$ |
| exo | R | exo | S | $R_p$ |
| exo | R | endo | R | $S_p$ |
| exo | R | endo | S | $S_p$ |
| exo | R | exo | S | $S_p$ |
| endo | S | exo | S | $R_p$ |
| endo | S | endo | R | $R_p$ |
| endo | S | exo | R | $R_p$ |
| endo | S | exo | S | $S_p$ |
| endo | S | endo | R | $S_p$ |
| endo | S | exo | R | $S_p$ |
| exo | S | endo | S | $R_p$ |
| exo | S | endo | R | $R_p$ |
| exo | S | exo | R | $R_p$ |
| exo | S | endo | S | $S_p$ |
| exo | S | endo | R | $S_p$ |
| exo | S | exo | R | $S_p$ |

wherein (1S)-exo-norbornyl is

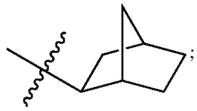 [SMILES: *C1CC2CCC1C2]

;

(1R)-exo-norbornyl is

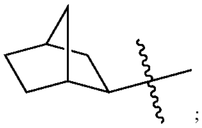 [SMILES: *C1CC2CCC1C2]

;

(1S)-endo-norbornyl is

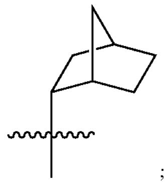 [SMILES: *C1CC2CCC1C2]

;

and (1R)-endo-norbornyl is

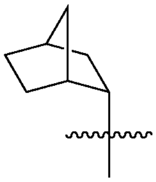

.

In some embodiments, the chiral phosphine ligand (L) according to Formula III or (L') according to Formula VI, wherein $R^5$ is norbornyl, comprises a single isomer selected from Table 1, or comprises a mixture of 2, 3, 4, or more isomers selected from Table 1.

EXAMPLES

Example 1: Asymmetric Hydrogenation of Compound 1

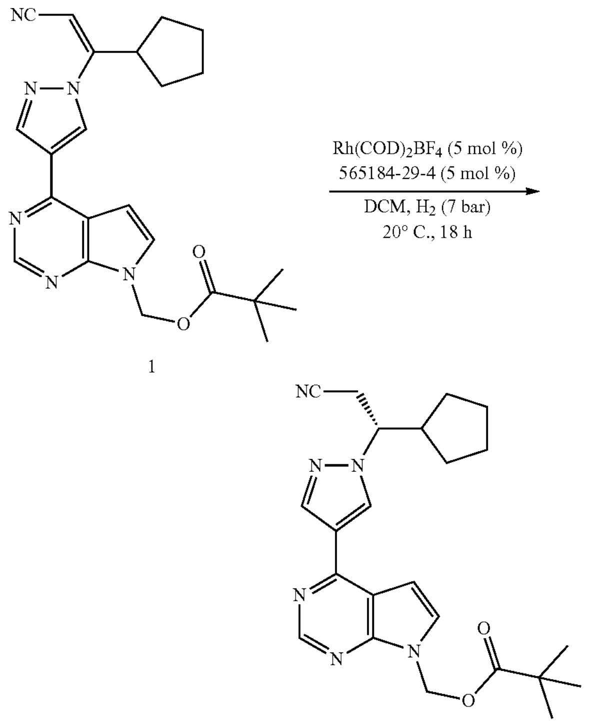

1

100
>99% conversion
95:5 er

A steel autoclave (200 mL) was charged with Compound 1 (400 mg, synthesized from procedures disclosed in U.S. Pat. No. 8,410,265), CAS #565184-29-4 (32 mg, 0.05 equiv, Aldrich), $Rh(COD)_2BF_4$ (19 mg, 0.05 equiv, Strem), and dichloromethane (DCM) (12.5 mL, 32 Vol). The autoclave was purged with hydrogen gas, then the reaction mixture was stirred at room temperature under hydrogen at 100 psi overnight for 18 hours, which resulted in >99% conversion by LC/MS. The reaction mixture was concentrated under reduced pressure, and then purified by column chromatography (silica, 1:10 to 1:1 gradient of ethyl acetate:heptane) to afford 373 mg (93% yield) of Compound 100 as an off-white solid. Chiral HPLC analysis (Chiralpak AD-H 4.6x250 mm, 5 μm, 70:30 hexanes: isopropanol with 0.1% diethyl amine, flow rate 1.0 ml/min) showed a 95:5 enantiomeric ratio, or 90% enantiomeric excess, favoring the (R)-enantiomer (4.7% for the first peak at 12.3 minutes, (S)-enantiomer; 95.2% for the second peak at 16.6 minutes, (R)-enantiomer). $^1H$-NMR (DMSO-$d_6$, 400 MHz): δ 8.83 (s, 1H), 8.78 (s, 1H), 8.39 (s, 1H), 7.74 (d, 1H), 7.11 (d, 1H), 6.24 (s, 2H), 4.54 (td, 1H), 3.21 (m, 2H), 2.45 (sextet, 1H), 1.16-1.85 (m, 8H), 1.08 (s, 9H).

Example 2: Asymmetric Hydrogenation of Compound 2

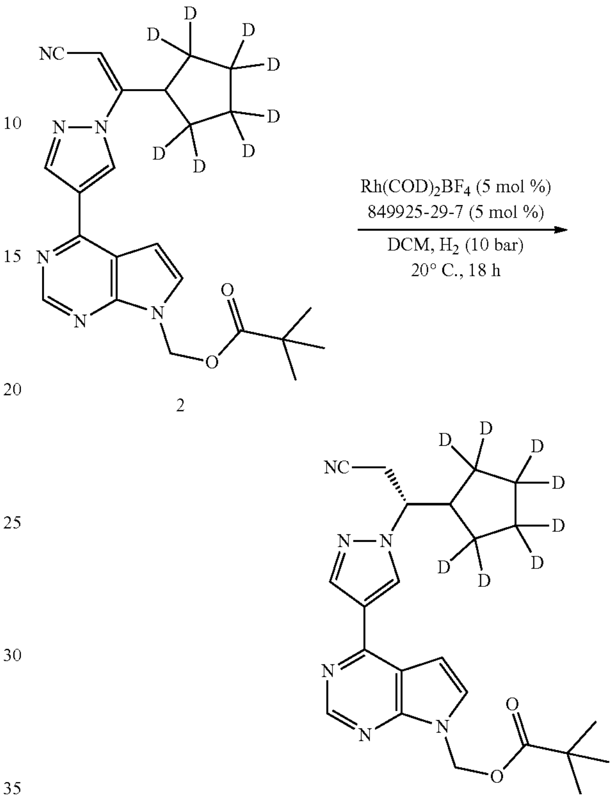

2

200
100% conversion
99:1 er

A reaction vessel was charged with Compound 2 (1 equiv), CAS #849925-29-7 (0.05 equiv, Sigma-Aldrich), $Rh(COD)_2BF_4$ (0.05 equiv, Strem), and dichloromethane (0.2 M solution). The reaction vessel was purged with hydrogen gas, then pressurized to 10 bar of hydrogen gas and stirred at room temperature overnight for 18 hours. The reaction vessel was then vented, and the reaction was quenched with a DMSO: MeCN (1:3) solution containing 10 mol % biphenyl as an internal standard. UPLC-MS analysis (Acquity HSS 1.8 μm C18, 50 mmx2.1 mm, 1.0 mL/min flow rate, MeCN: $H_2O$: 0.1% ammonium formate, 5% to 99% MeCN gradient) showed 100% conversion to Compound 200 having a major observed mass of 427. Chiral HPLC analysis showed a 99:1 enantiomeric ratio, or 98% enantiomeric excess, favoring the (R)-enantiomer.

Under the same reaction conditions, Compound 1 was hydrogenated using CAS #849925-29-7 and $Rh(COD)_2BF_4$ as catalyst. UPLC-MS analysis showed 100% conversion to Compound 100 having a major observed mass of 419. Chiral HPLC analysis showed a 98% enantiomeric excess of the (R)-enantiomer.

Under the same reaction conditions, Compound 2 was hydrogenated using CAS #565184-29-4 and $Rh(COD)_2BF_4$ as catalyst. UPLC-MS analysis showed 100% conversion to Compound 200 having a major observed mass of 427. Chiral HPLC analysis showed a 90% enantiomeric excess of the (R)-enantiomer.

Under the same reaction conditions, Compound 2 was hydrogenated using CAS #849925-29-7 and $Rh(COD)_2BF_4$ as catalyst and trifluoroethanol as solvent instead of DCM. UPLC-MS analysis showed 97% conversion to Compound 200 having a major observed mass of 427. Chiral HPLC analysis showed a 100% enantiomeric excess of the (R)-enantiomer.

Example 3: Asymmetric Hydrogenation of a Mixture of Compounds 1 and 3

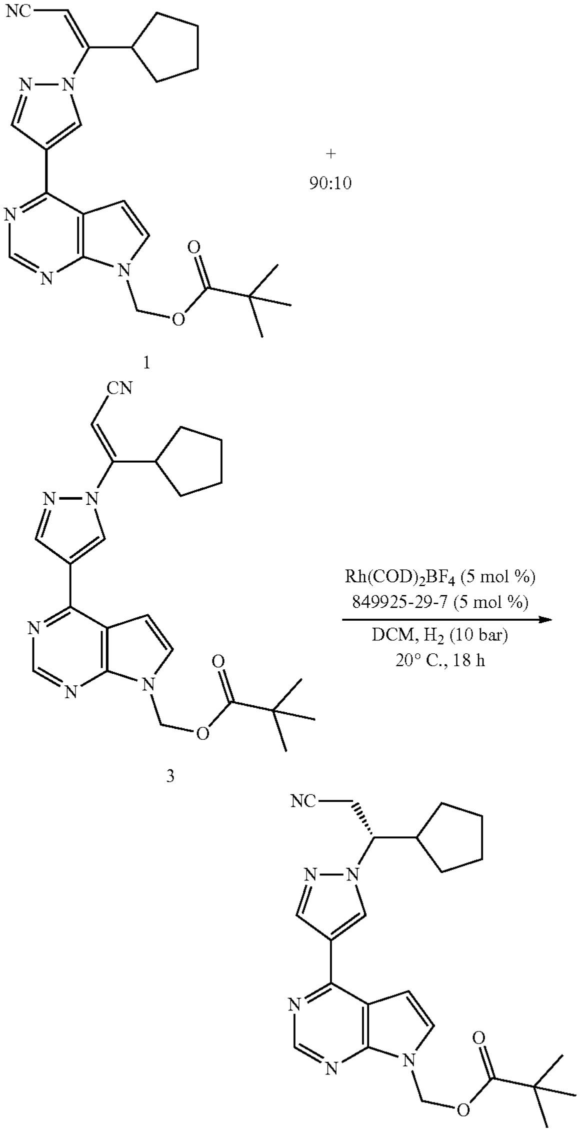

1

3

100
98% conversion
97:3 er

A reaction vessel was charged with a 90:10 mole ratio of Compound 1 to Compound 3 (1 equiv total), CAS #849925-29-7 (0.05 equiv, Aldrich), $Rh(COD)_2BF_4$ (0.05 equiv, Strem), and dichloromethane (0.2 M solution). The reaction vessel was purged with hydrogen gas, then pressurized to 10 bar of hydrogen gas and stirred at room temperature overnight for 18 hours. The reaction vessel was then vented, and the reaction was quenched with a DMSO: MeCN (1:3) solution containing 10 mol % biphenyl as an internal standard. UPLC-MS analysis showed 98% conversion to Compound 100 having a major observed mass of 419. Chiral HPLC analysis showed a 97:3 enantiomeric ratio, or 94% enantiomeric excess, of the (R)-enantiomer.

Example 4: Synthesis of Compound 2

Scheme 4
Preparation of a Compound of Formula II

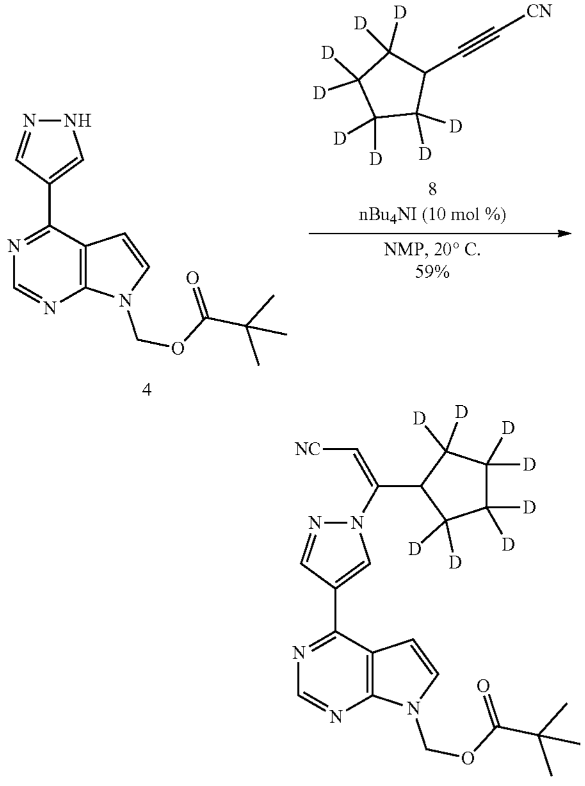

8

4

2

Scheme 4 discloses an exemplary preparation of a compound of Formula II wherein $Y^1$ is hydrogen, each $Y^2$ and each $Y^3$ is deuterium, and PG is pivaloyloxymethyl (POM). A reaction vessel was charged with Compound 4 (500 mg, 1 equiv, prepared according to the methods disclosed in U.S. Pat. No. 9,249,149 or U.S. Pat. No. 8,410,265), tetrabutylammonium iodide (62 mg, 10 mol %, Aldrich), and N-Methyl-2-pyrrolidone (NMP) (10 Vol, 5 mL). Then, Compound 8 in toluene was added (1.25 equiv, 28% w/w, 950 mg) and the reaction mixture was stirred at room temperature overnight. After 18 hours, the reaction was worked up by extracting with ethyl acetate, the organic layers were combined and washed with brine, dried over $MgSO_4$, filtered, and concentrated under reduced pressure to an oil. The product was purified by column chromatography (silica, 95:5 to 75:25 gradient of heptane: ethyl acetate), concentrated to a white solid, redissolved in acetone (2 mL) and recrystallized by addition of heptane (6 mL), and filtered to afford 409 mg (59% yield) of Compound 2 as a white powder. $^1H$-NMR (DMSO-$d_6$, 400 MHz): δ 9.12 (s, 1H), 8.87 (s, 1H), 8.65 (s, 1H), 7.82 (d, 1H), 7.20 (d, 1H), 6.27 (s, 2H), 5.85 (s, 1H), 3.32 (s, 2H), 1.10 (s, 9H).

Compound 8 was prepared according to Scheme 2 below.

Scheme 5
Synthesis of a Compound 8

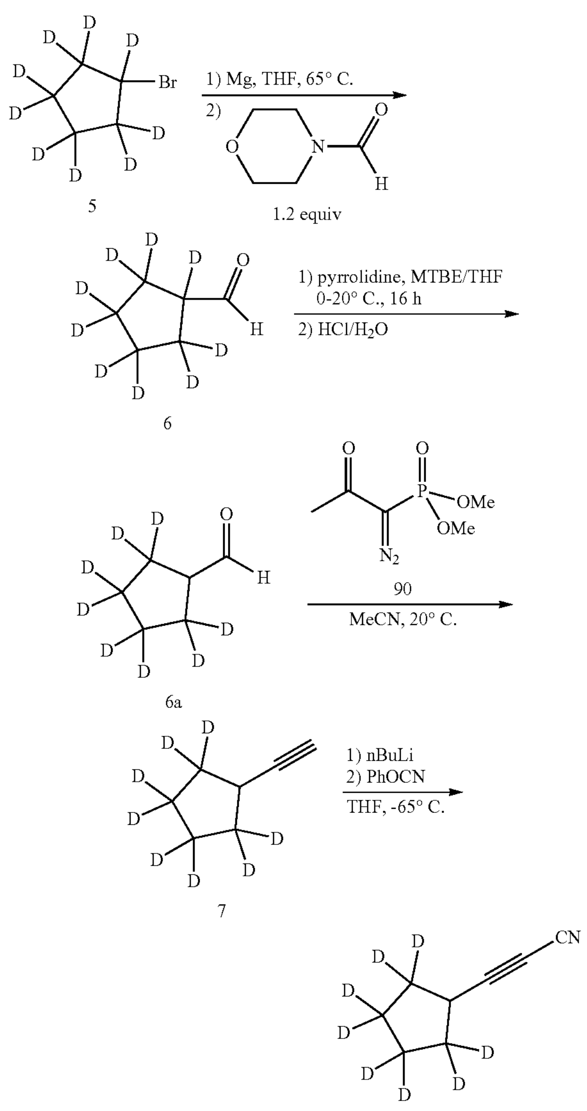

5
6
6a
90
7
8

Bromocyclopentane-$d_9$ 5 (16.0 kg, 1 equiv, 98 atom % D, Cambridge Isotope Labs) in tetrahydrofuran (THF, 2.9 vol), was added to magnesium turnings (3.0 kg, 1.2 equiv, Alfa Aesar) in THF (3.5 vol) heated to 60-65° C. and stirred for 1-2 hours to produce the corresponding Grignard reagent, which was then cooled to 0-5° C. N-Formyl morpholine (14.0 kg, 1.2 equiv, Melrob-Eurolabs) in THF (0.7 vol) was then added to the Grignard reagent and stirred for 1-2 hours. The reaction was quenched with aqueous HCl (7.5% w/w), the layers were separated, the aqueous phase was washed with t-butyl methyl ether (MTBE), and the organic layers were combined to afford crude Compound 6 in 65% yield by GC and $^1$H-NMR analysis.

Compound 6 (135.4 mol, 1 equiv) in THF/MTBE at 0° C. was treated with pyrrolidine (31.9 kg, 3.30 equiv, Molekula)), and then the reaction mixture was warmed to room temperature and stirred overnight to afford the pyrrolidine-derived enamine. Aqueous HCl (7.5% w/w) was added to regenerate the aldehyde, and then the layers were separated and the aqueous layer was extracted twice with MTBE. The organic phases were combined, washed with brine, and dried over $MgSO_4$, and filtered to afford crude Compound 6a in 71% yield by GC and $^1$H-NMR analysis. In some embodiments, the level of deuterium incorporation at the position equivalent to $Y^1$ is about 1-2%. In some embodiments, the level of deuterium incorporation at the position equivalent to $Y^1$ is at the natural isotopic abundance of deuterium.

Compound 6a (19.2 g, 8% w/w in MTBE/THF) diluted in MeOH (43 mL, 29 vol) was added to dimethyl (1-diazo-2-oxopropyl)phosphonate 90 (1.2 equiv) in acetonitrile (214 mL, 76 vol versus phosphonate) and the reaction mixture was stirred at room temperature for two days. The reaction mixture was diluted with water, the aqueous phase was extracted with heptane, and the combined organic phases were washed with brine, dried over $MgSO_4$, filtered, and purified by fractional distillation to afford compound 7 (0.49 g, 34% yield). $^1$H-NMR ($CDCl_3$, 500 MHz): δ 2.64 (s, 1H), 2.10 (s, 1H).

Dimethyl (1-diazo-2-oxopropyl)phosphonate 90 was provided by adding dimethyl-2-oxopropylphosphonate (2.85 g, 1.2 equiv, Aldrich) to a reaction vessel charged with potassium carbonate (5.9 g, 2.5 equiv, Aldrich) in acetonitrile (214 mL, 75 vol versus phosphonate) and tosyl azide (24.9 g, 14% in toluene 1.0 equiv versus phosphonate), and stirring for 6 hours at room temperature, after which the reaction was complete by LC/MS analysis. Phosphonate 90 in solution was then used as-is.

Compound 7 (0.49 g, 4.75 mmol, 42 mL solution) was diluted with THF (8 mL), cooled to −40° C. and treated with $nBuL_1$ (2.5 mL, 2.5 M in hexanes, 1.4 equiv, Aldrich). The reaction mixture was further cooled to −65° C. and then phenylcyanate (1.3 equiv) was added. The reaction mixture was stirred for 15 minutes, warmed to 0° C., quenched with NaOH solution, and the organic layer was separated, dried over $MgSO_4$, and concentrated to afford crude Compound 8 (0.44 g, 56% yield). MS (m/z): 125 $[M-D]^+$. $^1$H-NMR ($CDCl_3$, 400 MHz): δ 2.64 (s, 1H).

Phenyl cyanate was provided by adding triethylamine (0.9 mL, 1.4 equiv) to a 0° C. solution of phenol (0.59 g, 1.33 equiv) and cyanogenbromide (33.15 g, 1.4 equiv) in a mixture of n-hexane (3.0 mL, 5 Vol) and ethyl ether (1.5 mL, 2.5 Vol). The reaction mixture was warmed to room temperature, stirred for 45 minutes, cooled again to 0° C., and then treated with a solution of phenol (0.04 g, 0.1 equiv) in triethylamine (1.0 mL, 1.6 equiv). The reaction mixture was warmed to room temperature and stirred for 90 minutes more, and then filtered to provide phenyl cyanate solution which was used as-is.

Example 5: Synthesis of Compound 3

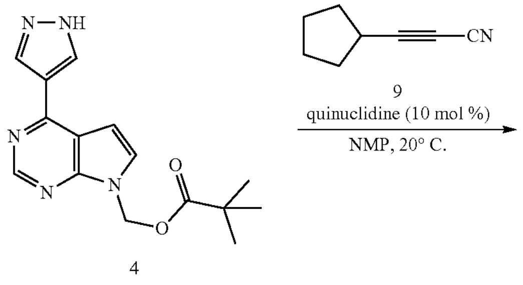

9
4

-continued

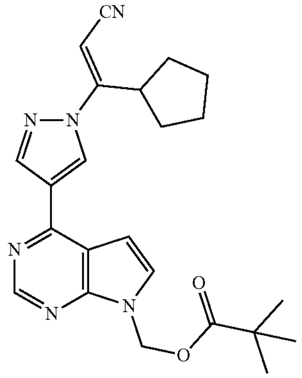

3

Example 5 discloses an exemplary preparation of a compound of Formula V wherein each of $Y^1$, $Y^2$, and $Y^3$ is hydrogen, and PG is pivaloyloxymethyl (POM). A reaction vessel was charged with Compound 4 (500 mg, 1 equiv, prepared according to the methods disclosed in U.S. Pat. No. 9,249,149 or U.S. Pat. No. 8,410,265), quinuclidine (20 mg, 10 mol %, Alfa Aesar), and N-Methyl-2-pyrrolidone (NMP) (5 Vol, 5 mL). Then, Compound 9 (1.25 equiv, 320 mg, prepared according to the methods disclosed in U.S. Pat. No. 8,410,265) was added and the reaction mixture was stirred at room temperature overnight. After 18 hours, the reaction was diluted with 5% aqueous NaCl, extracted with ethyl acetate, the organic layers were combined and washed with brine, dried over $MgSO_4$, filtered, and concentrated under reduced pressure to an oil. The product was purified by prep HPLC (Agilent Prep-$C_{18}$ Scalar, 21.2×50 mm, 10 μm, 50:50 to 5:95 gradient of 0.1% formic acid in water: MeCN, peak at 6.96 min), the fractions containing Compound 3 were combined and concentrated. The residue was partitioned between ethyl acetate and water, the organic layer was washed with water and brine, dried over $MgSO_4$, filtered, and concentrated to an oil. The oil was dissolved in dichloromethane and then re-concentrated to afford 36 mg (5% yield) of Compound 3 as a white solid.

Example 6: Synthesis of Compound 11

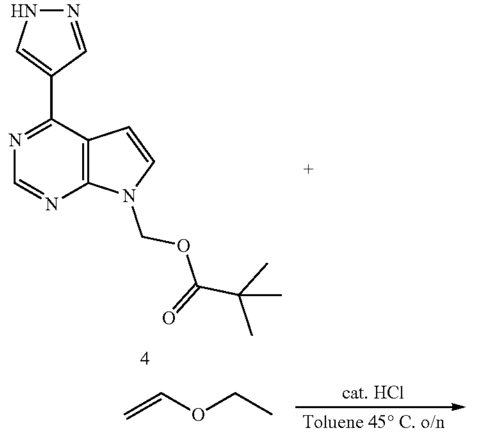

4

-continued

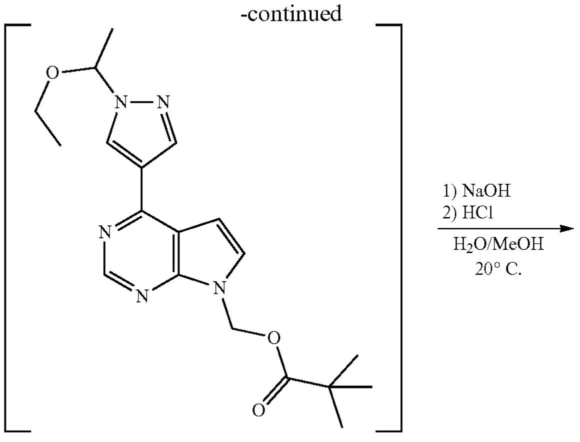

10

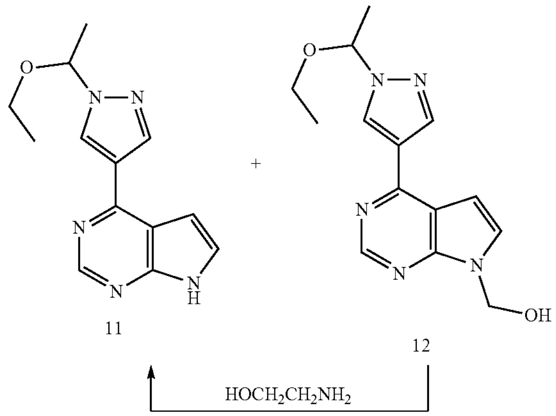

11

12

Compound 4 (250 g, 835.2 mmol, 1.0 equiv, prepared according to the methods described in U.S. Pat. No. 9,249,149 or U.S. Pat. No. 8,410,265) was dissolved in toluene (1500 mL, 6 Vol) and treated with ethyl vinyl ether (184 mL, 1921 mmol, 2.3 equiv) and HCl solution in cyclopentyl methyl ether (10 mL, 29.23 mmol, 0.04 equiv, 3 M solution). The resulting suspension was stirred at internal temperature 55° C. for two overnights.

LC/MS analysis showed complete conversion to Compound 10. The reaction mixture was cooled to ambient temperature and quenched by addition of sodium bicarbonate ($NaHCO_3$) solution (4% w/w, 250 mL, 1 Vol, 125.3 mmol, 0.15 equiv). The organic phase was separated, washed with water, and then distilled with concomitant addition of methanol to remove toluene. LC/MS analysis showed near-complete loss of toluene (98:2 Compound 10/toluene ratio at 254 nm).

To remove the POM protecting group from Compound 10, NaOH (2.0 N solution, 84 mL, 167 mmol, 0.2 equiv) was added, and the mixture was stirred for 60 min at ambient temperature. LC/MS analysis showing 99% conversion. The reaction was quenched by addition of a solution of ethanolamine (100 mL, 1670.4 mmol, 2.0 equiv) in HCl (1.0 N prior to ethanolamine addition, 250 mL, 250 mmol, 0.3 equiv). After 10 min stirring, LC/MS analysis showed complete conversion to Compound 11.

The reaction mixture was extracted with methyl tert-butyl ether (MTBE), washed with brine, and the organic layer was concentrated under vacuum to ~1 L. The batch was recrystallized, filtered, and dried to yield 108 g (50% yield) of Compound 11.

$^1$H-NMR (400 MHz, DMSO-d6) δ 12.10 (s, 1H), 8.77 (d, J=0.7 Hz, 1H), 8.68 (s, 1H), 8.34 (d, J=0.7 Hz, 1H), 7.58 (d, J=3.6 Hz, 1H), 7.02 (d, J=3.6 Hz, 1H), 5.67 (q, J=6.0 Hz, 1H), 3.49 (dq, J=9.6, 7.0 Hz, 1H), 3.26 (dq, J=9.6, 7.0 Hz, 1H), 1.69 (d, J=6.0 Hz, 3H), 1.06 (t, J=7.0 Hz, 3H).

Example 7: Synthesis of Compound 14

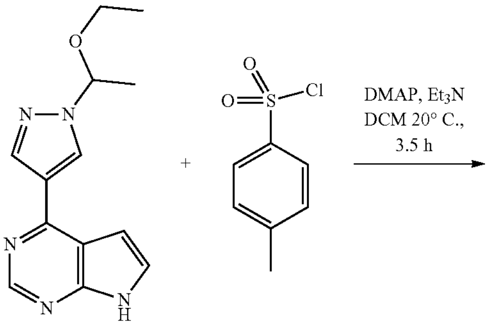

11

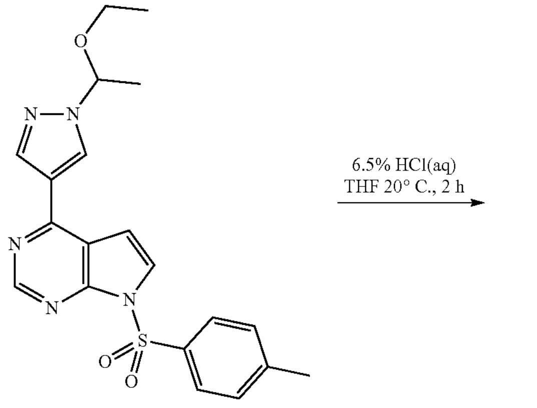

13

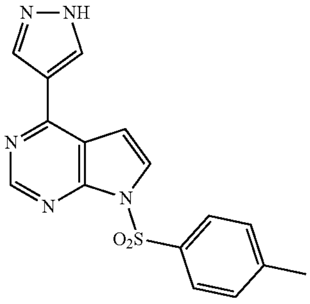

14

Compound 11 (25.0 g, 97.3 mmol, 1.0 equiv) was dissolved in dichloromethane (DCM, 160 mL, 6.4 volumes). Dimethylaminopyridine (DMAP, 1.20 g, 9.82 mmol, 0.10 equiv), triethylamine (Et3N, 18.0 mL, 129 mmol, 1.33 equiv), and then toluenesulfonyl chloride (TsCl, 20.4 g, 107 mmol, 1.10 equiv) in DCM (85 mL, 3.4 volumes) were added in succession. The reaction was stirred at 20° C. for 3.5 h, when 94% conversion of Compound 13 was detected. The reaction was quenched with deionized water, and the organic layer was worked up by washing with saturated aqueous $NaHCO_3$ and brine. The organic layer was separated, dried over $MgSO_4$, and concentrated to yield 37.9 g (94.6% yield) of Compound 13 as a foam to be used directly in the next reaction.

$^1$H NMR (400 MHz, DMSO-d6): δ 8.85 (s, 1H), 8.84 (d, J=0.7 Hz, 1H), 8.35 (d, J=0.6 Hz, 1H), 8.06-7.99 (overlap, 3H), 7.45 (dd, J=8.7, 0.8 Hz, 2H), 7.41 (d, J=4.1 Hz, 1H), 5.65 (q, J=6.0 Hz, 1H), 3.47 (dq, J=9.7, 7.0 Hz, 1H), 3.23 (dq, J=9.6, 7.0 Hz, 1H), 2.35 (s, 3H), 1.66 (d, J=6.0 Hz, 3H), 1.04 (t, J=7.0 Hz, 3H).

Compound 13 was dissolved in THF (200 mL, 5.3 volumes), and then HCl diluted to 6.5% (28 mL 37% HCl, 131 mL H2O) was added. The reaction was stirred at 20° C. for 2 hours, after which a solid had crashed out, presumed to be Compound 14-HCl salt. LC/MS confirmed the reaction had gone to completion. The reaction was then quenched by addition of aqueous saturated $Na_2CO_3$ (350 mL, brought to ~pH 8). The resultant slurry was filtered to remove solids, the solids were washed with water, triturated overnight in DCM, filtered, and dried to yield 25.5 g (81.6%) of Compound 14 as an off-white solid.

$^1$H NMR (400 MHz, DMSO-d6): δ 13.48 (s, 1H), 8.83 (s, 1H), 8.69 (s, 1H), 8.33 (s, 1H), 8.03 (d, J=8.4 Hz, 2H), 8.00 (d, J=4.1 Hz, 1H), 7.45 (d, J=7.8 Hz, 2H), 7.37 (d, J=4.1 Hz, 1H), 2.35 (s, 3H).

Example 8: Synthesis of Compound 15

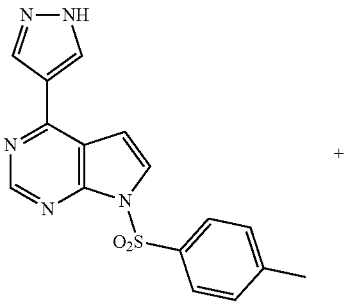

14

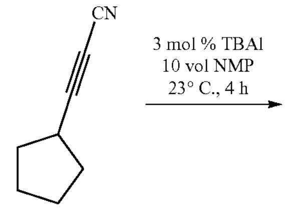

9

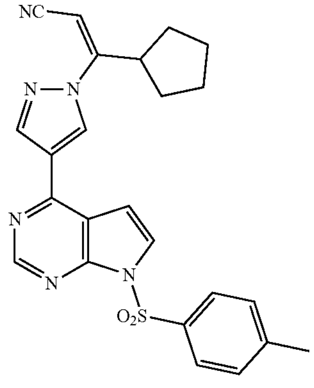

15

Compound 14 (500 mg, 1.47 mmol, 1.0 equiv) and tetrabutylammonium iodide (TBAI, 17 mg, 0.046 mmol, 0.0312 equiv) were dissolved in NMP (4.0 mL, 8 volumes). Compound 9 (221 mg, 1.63 mmol, 1.11 equiv, 88 wt % solution in hexane) was diluted in NMP (1.0 mL, 2 volumes) and then added to the solution of Compound 14. The reaction mixture was stirred under nitrogen for 4 hours, after which it had gone to >96% conversion. The reaction mixture was extracted with EtOAc, washed with water and brine, dried over $MgSO_4$, and concentrated to a foam which was triturated with EtOAc. The resultant solids were combined to yield 331 mg (49% yield) of Compound 15 as a white solid.

$^1$H NMR (400 MHz, DMSO-d6): δ 9.12 (s, 1H), 8.92 (s, 1H), 8.62 (s, 1H), 8.11 (d, J=4.1 Hz, 1H), 8.04 (d, J=8.5 Hz, 2H), 7.46 (d, J=8.2 Hz, 2H), 7.43 (d, J=4.1 Hz, 1H), 5.86 (d, J=1.2 Hz, 1H), 3.54 (p, J=8.0 Hz, 1H), 2.36 (s, 3H), 1.97-1.87 (overlap, 2H), 1.76-1.57 (overlap, 4H), 1.56-1.46 (overlap, 2H).

Example 9: Synthesis of Compound 300

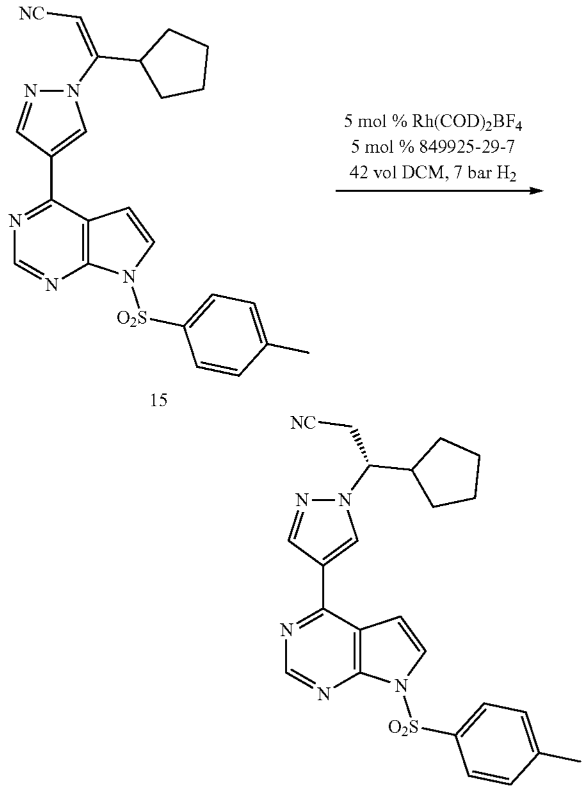

15

300

A hydrogenation reaction vessel was charged with Compound 15 (350 mg, 0.70 mmol, 1.0 equiv), Rh(I) catalyst (14 mg, 0.035 mmol, 0.05 equiv), ligand CAS #849925-29-7 (24 mg, 0.035 mmol, 0.05 equiv), and DCM (19.478 mL, 42 volumes). The reaction vessel was then pressurized with 7 bar (100 psi) $H_2$ gas and the reaction was stirred overnight at 20° C., after which LC/MS showed ~95% conversion. The reaction mixture was concentrated and purified by column chromatography (eluting with EtOAc/heptane) to yield 284 mg (88% yield) of Compound 300. Chiral HPLC analysis ((S,S) Whelk-o1 150×2.1 mm, 3.5 μm, 85:15 hexane to 1:1 ethanol/methanol with 0.1% diethylamine, flow rate 0.75 mL/min) showed a 98:2 enantiomeric ratio, or 96% enantiomeric excess, favoring the (R)-enantiomer (98.3% for the first peak at 7.36 min, (R)-enantiomer, and 1.7% for the second peak at 8.02 min, (S)-enantiomer).

$^1$H NMR (400 MHz, DMSO-d6) δ 8.86 (d, J=0.8 Hz, 1H), 8.84 (s, 1H), 8.38 (s, 1H), 8.06 (d, J=4.1 Hz, 1H), 8.02 (d, J=8.4 Hz, 2H), 7.45 (d, J=7.8 Hz, 2H), 7.36 (d, J=4.1 Hz, 1H), 4.51 (td, J=9.6, 4.4 Hz, 1H), 3.25 (dd, J=17.2, 9.4 Hz, 1H), 3.18 (dd, J=17.2, 4.4 Hz, 1H), 2.39 (m, 1H), 2.35 (s, 3H), 1.80 (m, 1H), 1.67-1.38 (overlap, 4H), 1.37-1.21 (overlap, 2H), 1.17 (m, 1H).

Example 10: Synthesis of Compound 16

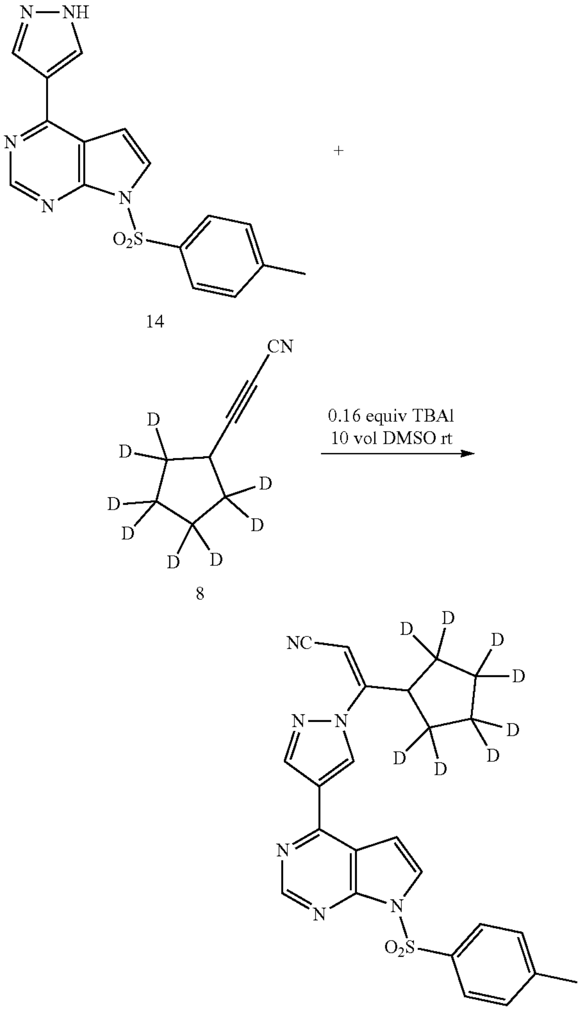

14

8

16

Compound 16 was prepared according to the methods described above for Compound 15 starting with Compound 14 (600 mg, 1.77 mmol, 1.0 equiv) and Compound 8 (499 mg, 1.94 mmol, 1.10 equiv, 50 wt % solution in hexane/toluene).

The reaction mixture was stirred overnight (>99% conversion), extracted with EtOAc, washed with brine and water, dried over $MgSO_4$, filtered and concentrated to an oil which was triturated with EtOAc. The resultant solid was filtered and dried to yield 366 mg (44% yield) of Compound 16. The mother liquor was concentrated and purified by ISCO CombiFlash automated chromatography. Fractions containing Compound 16 were concentrated and triturated with EtOAc. The resultant solid was filtered and dried to yield 135 mg of Compound 16. The product crops were combined for a total yield of 501 mg (60.7%) as a white solid.

$^1$H NMR (400 MHz, DMSO-d6): δ 9.12 (s, 1H), 8.92 (s, 1H), 8.62 (s, 1H), 8.11 (d, J=4.1 Hz, 1H), 8.04 (d, J=8.5 Hz, 2H), 7.46 (d, J=7.9 Hz, 2H), 7.43 (d, J=4.1 Hz, 1H), 5.85 (d, J=1.3 Hz, 1H), 3.51 (s, 1H), 2.36 (s, 3H).

Example 11: Synthesis of Compound 400

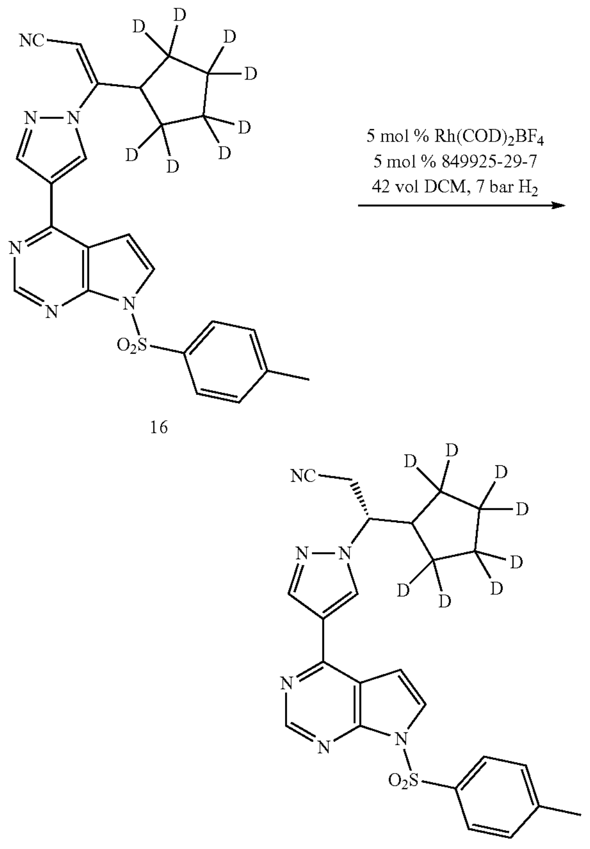

16

400

Compound 400 was prepared according to the methods described above for Compound 300.

After stirring overnight, LC/MS analysis showed complete conversion and 97.8% AUC of product. The reaction mixture was concentrated and purified by column chromatography (eluting with EtOAc/heptane) to yield 318 mg (95%) of Compound 400.

Chiral HPLC analysis showed 99:1 enantiomeric ratio, or 98% enantiomeric excess, favoring the (R)-enantiomer (98.7% of the first peak at 7.50 min, (R)-enantiomer, and 1.3% of the second peak at 8.16 min, (S)-enantiomer).

$^1$H NMR (400 MHz, DMSO-d6): δ 8.86 (d, J=0.7 Hz, 1H), 8.84 (s, 1H), 8.38 (s, 1H), 8.06 (d, J=4.1 Hz, 1H), 8.02 (d, J=8.4 Hz, 2H), 7.45 (d, J=8.0 Hz, 2H), 7.36 (d, J=4.1 Hz, 1H), 4.51 (td, J=9.6, 4.4 Hz, 1H), 3.25 (dd, J=17.2, 9.5 Hz, 1H), 3.17 (dd, J=17.2, 4.4 Hz, 1H), 2.38-2.35 (overlap, 4H).

Example 12: Increasing the Enantiomeric Excess of Compound 400

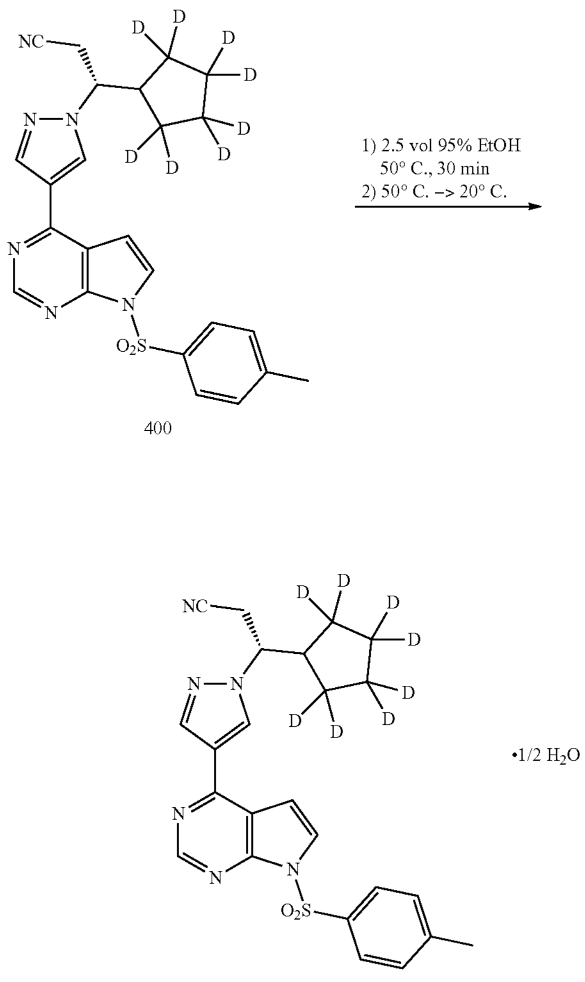

400

•1/2 $H_2O$

500

Compound 400 was dissolved in 2.5 vol 95% EtOH (5% water) and heated to 50° C. After 37 minutes at 50° C., solid crashed out. After cooling to 20° C. and stirring overnight, the solid was vacuum filtered and the flask washed thrice with 1 vol 200 proof EtOH. Both the solid precipitate and mother liquor were analyzed for chiral purity. The solid, hemihydrate Compound 500, as indicated by KF and TGA water content measurements, had upgraded to 99.5:0.5 enantiomeric ratio, or 99% enantiomeric excess, favoring the (R)-enantiomer (99.5% of the first peak at 7.46 min, (R)-enantiomer, and 0.5% of the second peak at 8.05 min, (S)-enantiomer), with an 87.8% recovery. The mother liquor subsequently downgraded to 78:22 enantiomeric ratio, or 56% enantiomeric excess, favoring the (R)-enantiomer (78.3% of the first peak at 7.39 min, (R)-enantiomer, and 21.7% of the second peak at 8.04 min, (S)-enantiomer).

$^1$H NMR (400 MHz, DMSO-d6): δ 8.85 (d, J=0.7 Hz, 1H), 8.84 (s, 1H), 8.38 (s, 1H), 8.05 (d, J=4.1 Hz, 1H), 8.02 (d, J=8.4 Hz, 2H), 7.45 (d, J=7.7 Hz, 2zH), 7.35 (d, J=4.1 Hz, 1H), 4.51 (td, J=9.6, 4.4 Hz, 1H), 3.25 (dd, J=17.1, 9.4 Hz, 1H), 3.17 (dd, J=17.1, 4.4 Hz, 1H), 2.38-2.35 (overlap, 4H).

Example 13: Synthesis of Compound 700

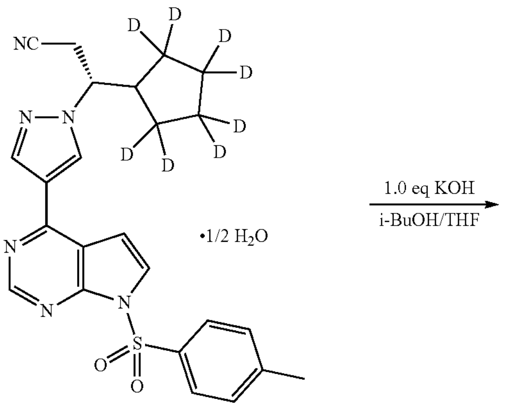

500

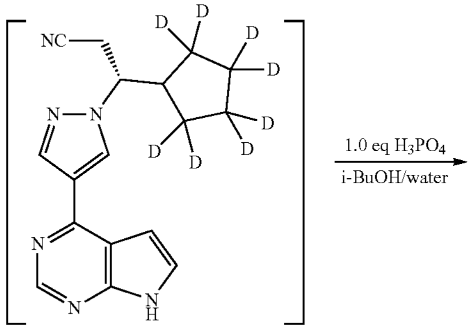

600

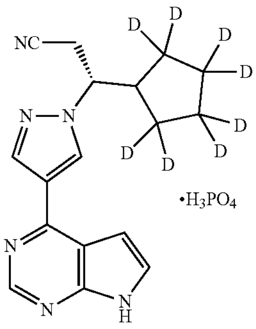

700

A solution of Compound 500 (5.00 g, 10.5 mmol, 1.00 eq) in anhydrous THF (20.0 mL, 4.00 vol) was added to a solution of KOH (0.590 g, 10.5 mmol, 1.00 eq) in i-BuOH (14.2 mL, 2.84 vol) at ≤5° C. After stirring at room temperature for 2 hours, LC-MS analysis showed 99.5% conversion to Compound 600 (CTP-543). Water was added to the reaction mixture. The organic layer was separated from the aqueous layer, and then washed with a mixture of water and brine. The organic layer was partially concentrated under reduced pressure at 70° C. to give a light green cloudy solution (12.8 g, 2.56 wt), which was filtered, and then the total weight was adjusted to 25.0 g (5.00 wt) with i-BuOH. Water (2.64 mL, 0.528 vol) was added and the orange clear solution was warmed to 70-80° C. A portion of 85.7% $H_3PO_4$ (0.710 mL, 10.5 mmol, 1.00 eq) was added, and stirring for 10 min gave a suspension. Another portion of 85.7% $H_3PO_4$ (0.618 mL, 9.14 mmol, 0.870 eq) was added, and the suspension was stirred for 1 h at 70-80° C. The reaction mixture was then cooled to room temperature and stirred for 8 h. The suspension was filtered and dried to give Compound 700 (CTP-543 phosphate salt) as white powder (4.05 g, 93.4% yield).

$^1$H-NMR (400 MHz, $CD_3OD$): δ 1.22-1.92 (0.17H, m), 2.52 (1H, d), 3.13 (1H, dd), 3.25 (1H, dd), 4.51 (1H, dt), 7.02 (1H, d), 7.58 (1H, d), 8.42 (1H, s), 8.71 (1H, d), 8.71 (1H, s).

Example 14: Synthesis of Compound 18

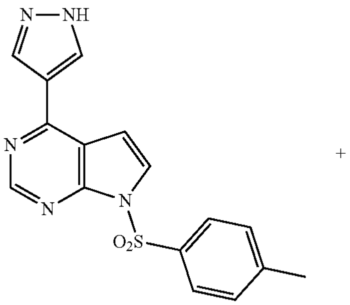

14

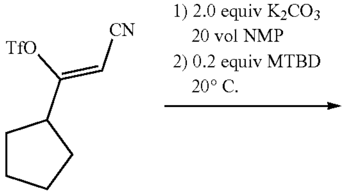

17

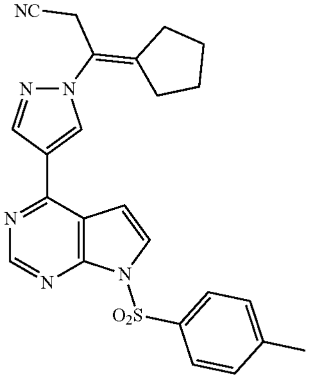

18

To a 500 mL Chemglass reactor with overhead stirrer was added solid Compound 14 (1.0 equivalents, 25.5 g, 75.2 mmol) and $K_2CO_3$ (2.0 equivalents, 20.8 g, 150 mmol). To the reactor was then added NMP (9.8 vol, 250 mL) and the stirrer turned on. The reactor was hooked up to a chiller set at 20° C. To the reactor was then added enol triflate 17 (1.0 equivalents, 22.0 g, 75.2 mmol). Enol triflate 17 may be prepared according to procedures disclosed in U.S. patent application 62/850,981. The bottle that contained the enol triflate was rinsed with twice with 10 mL NMP and transferred to the reactor. The remaining 240 mL NMP were added to the reactor (for a total of 20 volumes) and the reaction was allowed to stir at 20° C. After 72 hours, to the reaction was added 1-methyl-2,3,4,6,7,8-hexahydropyrimido[1,2-a]pyrimidine (MTBD, 0.1 equivalents, 1.08 mL, 7.5 mmol). After 2.5 hours, an additional 0.1 equiv MTBD was added. After 2 hours, the reaction was quenched by addition of 250 mL (10 vol) water and allowed to stir for 16 hours. The slurry was drained from the reactor and vacuum filtered through a 500 mL disposable funnel. The reactor was washed with 3 vol 2:1 NMP/water, which was then used to wash the cake. After 1 h drying on the funnel, the cake was washed with twice with 3 vol heptane. The washed cake was left to dry on the filter under vacuum. HPLC analysis of the still wet cake showed ~90% purity of desired product. To purge impurities, the cake was transferred to a 500 mL erlenmeyer and triturated with 5 vol (125 mL) EtOAc for 2 hours. The EtOAc slurry was filtered, washed with 1 vol (25 mL) EtOAc, and dried under vacuum. The product Compound 18 was obtained as a solid (22.7 g, 64% yield).

$^1H$ NMR (400 MHz, Acetone-d6) δ 8.83 (s, 1H), 8.69 (d, J=0.7 Hz, 1H), 8.41 (d, J=0.7 Hz, 1H), 8.12 (d, J=8.6 Hz, 2H), 7.93 (d, J=4.1 Hz, 1H), 7.45 (dd, J=8.6, 0.7 Hz, 2H), 7.27 (d, J=4.1 Hz, 1H), 3.87 (s, 2H), 2.62 (m, 2H), 2.47 (m, 2H), 2.39 (s, 3H), 1.84 (m, 2H), 1.72 (m, 2H).

Example 15: Synthesis of Compound 20

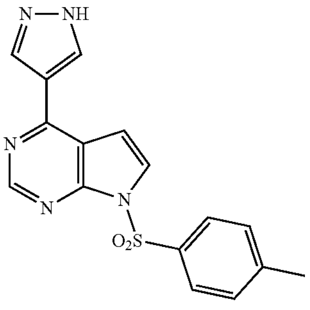

14

+

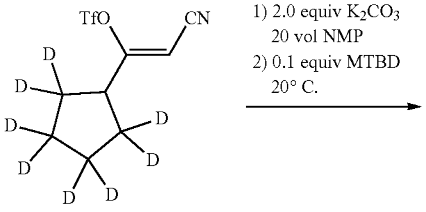

19

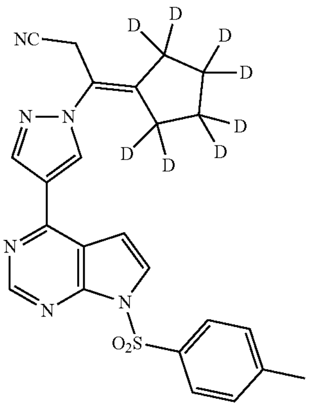

20

The product was prepared according to the methods described above for Compound 18 starting with heterocycle 14 (1.0 g, 2.95 mmol, 1.0 equiv) and enol triflate 19 (824 mg, 2.97 mmol, 1.0 equiv). Enol triflate 19 may be prepared according to procedures disclosed in U.S. patent application 62/850,981. The combined product Compound 20 was obtained in 807 mg (58.7%) as a solid.

$^1H$ NMR (400 MHz, DMSO-d6) δ 8.87 (s, 1H), 8.84 (d, J=0.7 Hz, 1H), 8.46 (d, J=0.7 Hz, 1H), 8.07-8.00 (overlap, 3H), 7.46 (d, J=7.8 Hz, 2H), 7.42 (d, J=4.1 Hz, 1H), 3.92 (s, 2H), 2.36 (s, 3H).

Example 16: Synthesis of Compound 400

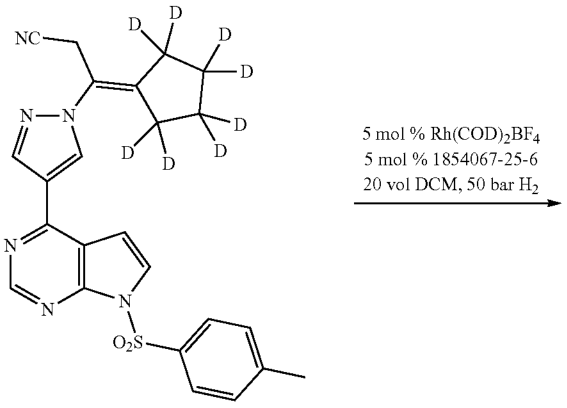

20

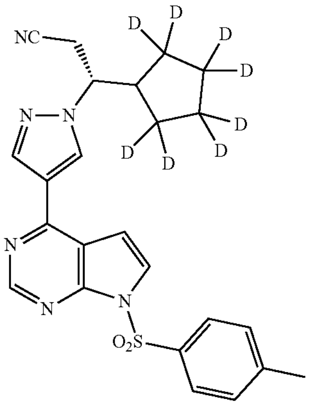

400

To a 10 mL vial was added Ts-cyclopentylidene-d8 20 (99.8 mg, 0.214 mmol, 1.0 equiv), Rh(I) catalyst (4.3 mg, 0.011 mmol, 0.05 equiv), and ligand CAS #1854067-25-6 (7.2 mg, 0.011 mmol, 0.05 equiv). To the vial was then added DCM (2.0 mL, 20 volumes) and it was sealed in a CAT 7 hydrogenation reactor. The reactor was purged 3 times with 10 bar H2 gas and then pressurized to 50 bar. The reaction was allowed to stir for 65 hours at room temperature and then the system was vented. Reaction progress was monitored by LCM showing ~98% conversion to desired product. The crude material was purified by ISCO CombiFlash automated chromatography, elution with EtOAc/heptane. Fractions containing the major peak were pooled, concentrated, and dried under vacuum. The product was obtained in 84 mg (84%) as a foam. A small sample was diluted in EtOH and analyzed by chiral HPLC ((S,S) Whelk-ol 150×2.1 mm, 3.5 □m, 85:15 hexane to 1:1 ethanol/methanol with 0.1% diethylamine, flow rate 0.75 mL/min)

and showed 94:6 enantiomeric ratio, or 88% enantiomeric excess, favoring the (R)-enantiomer.

$^1H$ NMR (400 MHz, DMSO-d6) δ 8.86 (d, J=0.7 Hz, 1H), 8.84 (s, 1H), 8.38 (s, 1H), 8.06 (d, J=4.1 Hz, 1H), 8.02 (d, J=8.5 Hz, 2H), 7.45 (d, J=8 Hz, 2H), 7.36 (d, J=4.1 Hz, 1H), 4.51 (td, J=9.6, 4.4 Hz, 1H), 3.25 (dd, J=17.1, 9.4 Hz, 1H), 3.17 (dd, J=17.2, 4.4 Hz, 1H), 2.37 (d, J=11.7 Hz, 1H), 2.35 (s, 3H).

Example 17: Synthesis of Compound 600

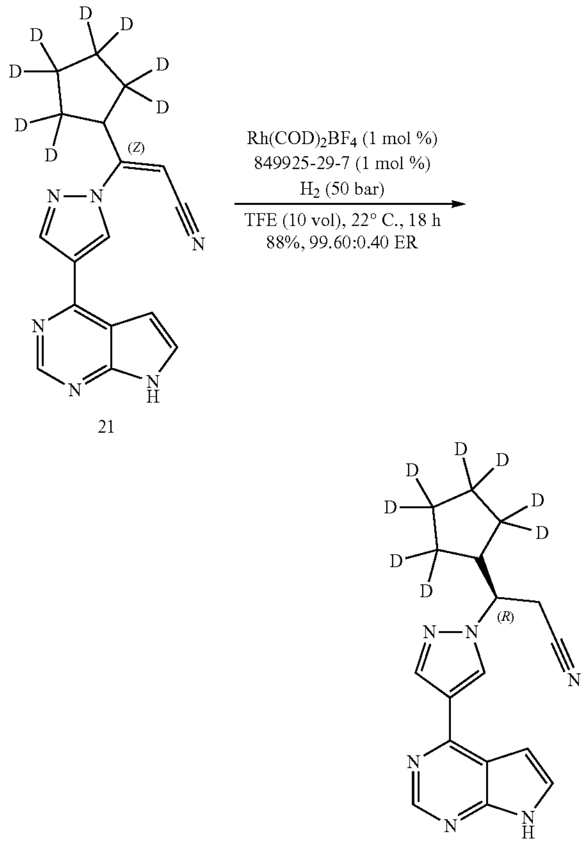

21

600

To a 10 mL glass vial with a stirbar was charged Compound 21 (95 mg), followed by a solution of ligand CAS #849925-29-7 (2.44 mg, 0.01 eq) and Bis(1,5-cyclooctadiene) rhodium (I) tetrafluoroborate (1.43 mg, 0.01 eq) in trifluoroethanol (1 mL) that had been prepared immediately before use. The glass vial was transferred to an autoclave and stirred under 50 bar of hydrogen gas at ambient temperature for 18 hours. After the reduction was determined to be complete, solvent was dried from the reaction mixture with a stream of nitrogen until thick residue was obtained. Methyl tert-butyl ether (1 mL) was charged to the vial and the mixture was concentrated by rotary evaporator to provide Compound 600 (CTP-543) as a brittle orange foam containing some residual solvents (109 mg, 77 wt %, 89% yield, 99.6:0.4 R/S enantiomeric ratio by chiral HPLC).

LRMS (ESI, $[M+H]^+$) calculated for $C_{17}H_{11}D_8N_6$=315.2; found=315.3 (conformed to reference)

$^1H$ NMR (400 MHz, $CDCl_3$) § 10.78 (s, 1H), 8.86 (s, 1H), 8.39 (s, 1H), 8.34 (s, 1H), 7.43 (s, 1H), 6.80 (s, 1H), 4.28 (m, 1H), 3.14 (dd, J=16.9, 8.3 Hz, 3H), 2.96 (dd, J=16.9, 3.5 Hz, 1H), 2.57 (d, J=9.8 Hz, 1H).

Example 18: Synthesis of Compound 600

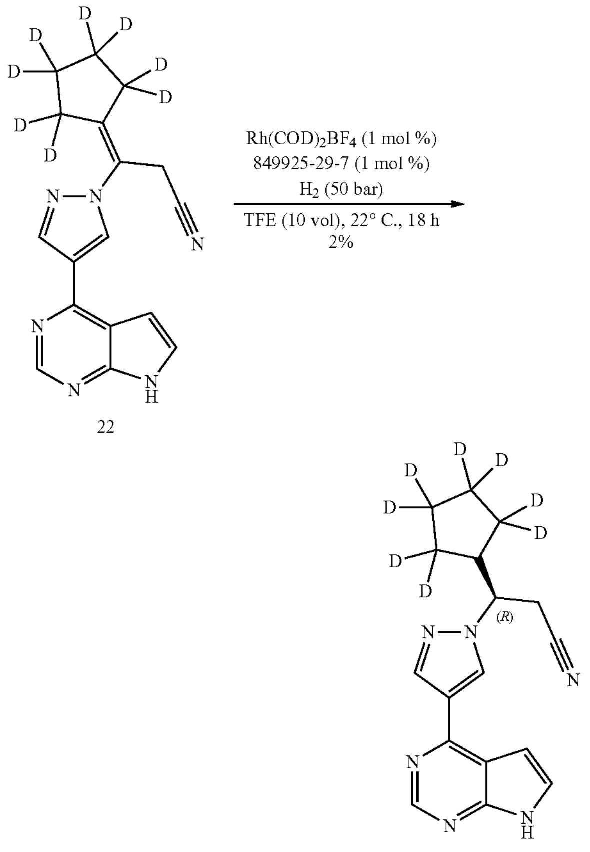

22

600

To a 10 mL glass vial with a stirbar was charged Compound 22 (114 mg), followed by a solution of ligand CAS #849925-29-7 (2.44 mg, 0.01 eq) and Bis(1,5-cyclooctadiene) rhodium (I) tetrafluoroborate (1.43 mg, 0.01 eq) in trifluoroethanol (1 mL) that had been prepared immediately before use. The glass vial was transferred to an autoclave and stirred under 50 bar of hydrogen gas at ambient temperature for 18 hours. Analysis of a sample of the reaction mixture by HPLC indicated 2% conversion to Compound 600 (CTP-543) by area (254 nm), and the mass of Compound 600 was found by HPLC-MS. Chiral HPLC indicated that the correct enantiomer was made (conformed to reference), although enantiomeric ratio was not determined.

LRMS (ESI, $[M+H]^+$) calculated for $C_{17}H_{11}D_8N_6$=315.2, found=315.3 (conformed to reference)

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. The relevant teachings of all patents, published applications and references cited herein are incorporated by reference in their entirety.

What is claimed is:

1. A process for preparing a compound of Formula I:

Formula I

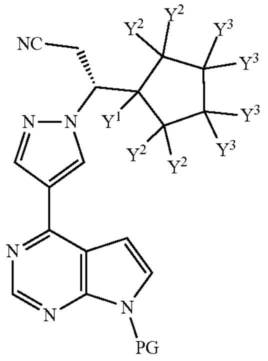

wherein:

$Y^1$ is H or D;

each $Y^2$ is H or D, wherein each $Y^2$ is identical;

each $Y^3$ is H or D, wherein each $Y^2$ is identical; and (i) PG is H; or (ii) PG is a protecting group selected from:

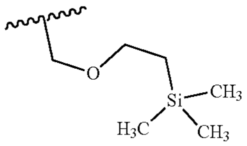
(SEM),

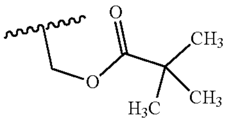
(POM),

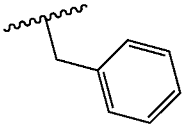
(Bn),

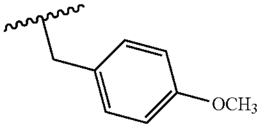
(PMB),

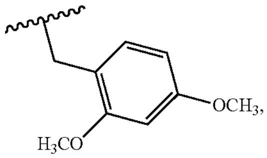

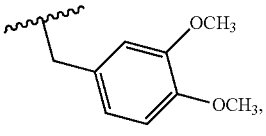
(DMPM)

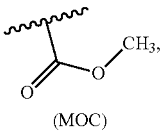
(MOC)

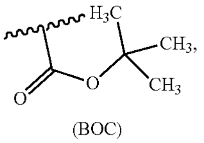
(BOC)

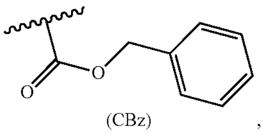
(CBz),

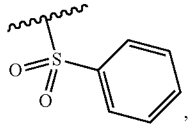

-continued

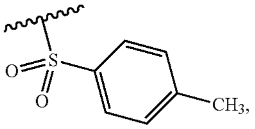
(Ts)

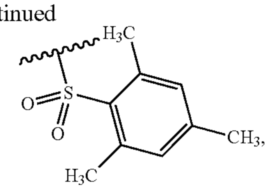

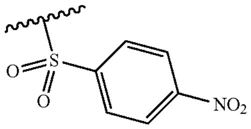
(p-nosyl), or

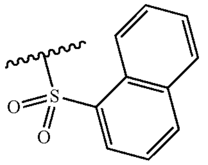
(1-napsyl);

wherein the process comprises:

(a) reacting a compound of Formula II:

Formula II

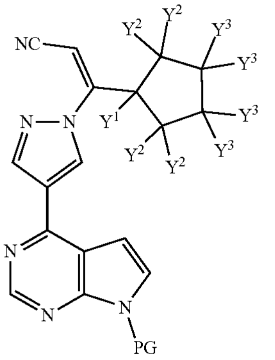

wherein each of $Y^1$, $Y^2$, $Y^3$, and PG in Formula II is defined as in Formula I;

with hydrogen gas in the presence of a hydrogenation catalyst comprising rhodium and a chiral phosphine ligand, (L), according to Formula III:

Formula III

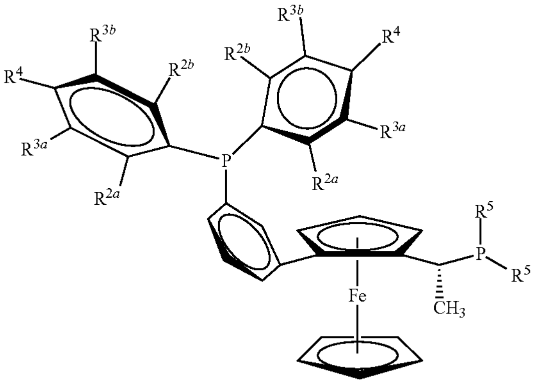

wherein:

$R^{2a}$ is independently H, $CH_3$, $CF_3$, or $OCH_3$;

$R^{2b}$ is independently H, $CH_3$, $CF_3$, or $OCH_3$;

$R^{3a}$ is independently H, $CH_3$, $CF_3$, or $OCH_3$;

$R^{3b}$ is independently H, $CH_3$, $CF_3$, or $OCH_3$;

$R^4$ is independently H, $CH_3$, $CF_3$, or $OCH_3$; and $R^5$ is independently alkyl or cycloalkyl, wherein alkyl is independently secondary or tertiary;

to provide the compound of Formula I above; or (b) reacting a compound of Formula VII:

Formula VII

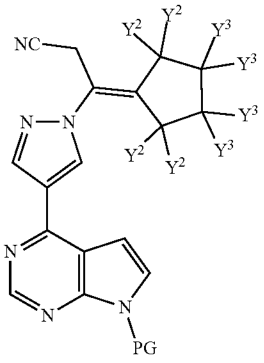

wherein each of $Y^2$, $Y^3$, and PG in Formula VII is defined as in Formula I;

with hydrogen gas in the presence of a hydrogenation catalyst comprising rhodium and a chiral phosphine ligand according to Formula VI:

Formula VI

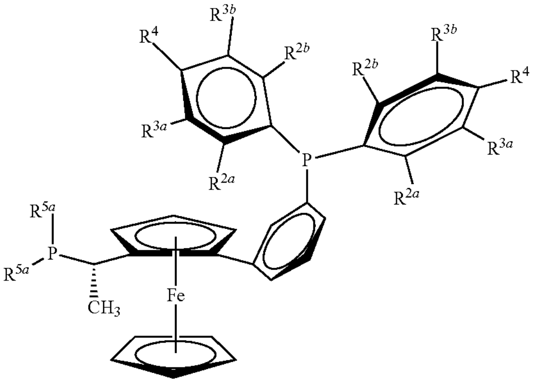

wherein:

each of $R^{2a}$, $R^{2b}$, $R^{3a}$, $R^{3b}$, and $R^4$ in Formula VI is defined as in Formula III; and each $R^{5a}$ is phenyl;

to provide the compound of Formula I above; or (c) reacting a compound of Formula VII:

Formula VII

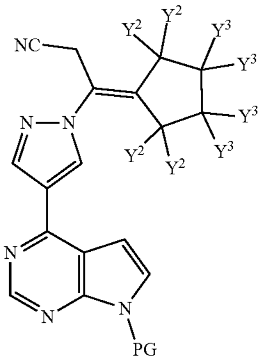

wherein each of $Y^2$, $Y^3$, and PG in Formula VII is defined as in Formula I;

with hydrogen gas in the presence of a hydrogenation catalyst comprising rhodium and a chiral phosphine ligand according to Formula VIII:

Formula VIII

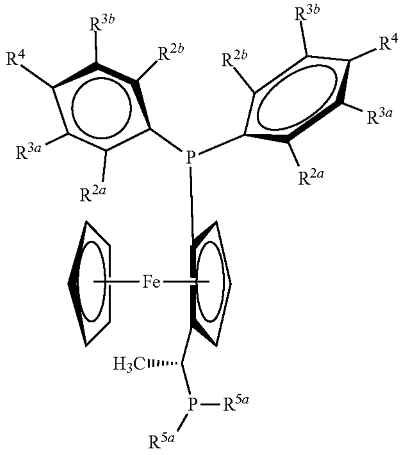

wherein:

each of $R^{2a}$, $R^{2b}$, $R^{3a}$, $R^{3b}$, and $R^4$ in Formula VIII is defined as in Formula III; and each $R^{5a}$ is $C(CH_3)_3$;

to provide the compound of Formula I above.

2. The process according to claim 1, wherein:

(a) $Y^1$ is H;
each $Y^2$ is H; and
each $Y^3$ is H; or (b) $Y^1$ is H;
each $Y^2$ is D; and
each $Y^3$ is D.

3. The process according to claim 1, wherein:

(i) PG is H; or (ii) PG is (Ts)

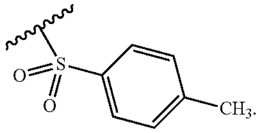

4. The process according to claim 1, wherein:

(a) $R^{2a}$ is independently H;
$R^{2b}$ is independently H;
$R^{3a}$ is independently H;
$R^{3b}$ is independently H; and
$R^4$ is independently H; or (b) $R^{2a}$ is independently H;
$R^{2b}$ is independently H;
$R^{3a}$ is independently $CH_3$ or $CF_3$;
$R^{3b}$ is independently $CH_3$ or $CF_3$; and
$R^4$ is independently H; or (c) $R^{2a}$ is independently H;
$R^{2b}$ is independently H;
$R^{3a}$ is independently $CH_3$;
$R^{3b}$ is independently $CH_3$; and
$R^4$ is independently $OCH_3$; or (d) $R^{2a}$ is independently H;
$R^{2b}$ is independently H;
$R^{3a}$ is independently H;
$R^{3b}$ is independently H; and
$R^4$ is independently $CH_3$, $CF_3$, or $OCH_3$; or
(e) $R^{2a}$ is independently H;
$R^{2b}$ is independently $CH_3$;
$R^{3a}$ is independently H;
$R^{3b}$ is independently H; and
$R^4$ is independently H.

5. The process according to claim 1, wherein $R^5$ is independently $C(CH_3)_3$, cyclopentyl, cyclohexyl, or norbornyl.

6. The process according to claim 1, wherein:
$R^{2a}$ is independently H;
$R^{2b}$ is independently H;
$R^{3a}$ is independently H;
$R^{3b}$ is independently H;
$R^4$ is independently H; and
$R^5$ is independently cyclohexyl or norbornyl.

7. The process according to claim 1, wherein the process comprises:
(a) reacting a compound of Formula II:

Formula II

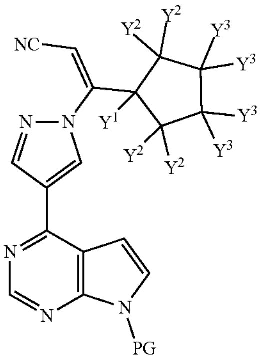

wherein each of $Y^1$, $Y^2$, $Y^3$, and PG in Formula II is defined as in Formula I;
with hydrogen gas in the presence of a hydrogenation catalyst comprising rhodium and a chiral phosphine ligand, (L), according to Formula III:

Formula III

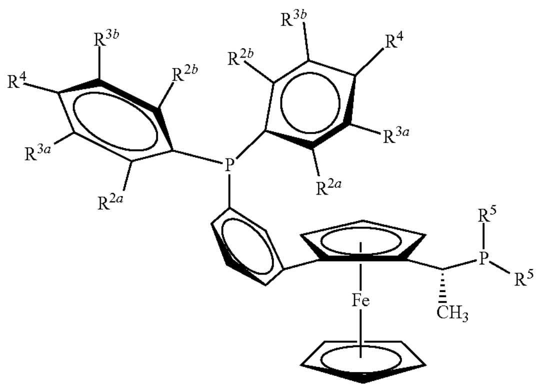

wherein:
$R^{2a}$ is independently H, $CH_3$, $CF_3$, or $OCH_3$;
$R^{2b}$ is independently H, $CH_3$, $CF_3$, or $OCH_3$;
$R^{3a}$ is independently H, $CH_3$, $CF_3$, or $OCH_3$;
$R^{3b}$ is independently H, $CH_3$, $CF_3$, or $OCH_3$;
$R^4$ is independently H, $CH_3$, $CF_3$, or $OCH_3$; and
$R^5$ is independently alkyl or cycloalkyl, wherein alkyl is independently secondary or tertiary;
wherein the hydrogenation catalyst comprising rhodium and the chiral phosphine ligand, (L), according to Formula III is formed by mixing the chiral phosphine ligand, (L), according to Formula III above with a rhodium pre-catalyst of the following formula:

$[Rh(L_1)(L_2)]^+NC^-$, wherein:
(i) $L_1$ is a pair of monodentate ligands, wherein the pair of monodentate ligands is a pair of identical alkene ligands or a pair of identical solvent ligands; or $L_1$ is a bidentate ligand, wherein the bidentate ligand is a diene ligand;
(ii) $L_2$ is a pair of monodentate ligands, wherein the pair of monodentate ligands is a pair of identical alkene ligands or a pair of identical solvent ligands; or
$L_2$ is a bidentate ligand, wherein the bidentate ligand is a diene ligand; and
$NC^-$ is a non-coordinating counterion selected from the group consisting of $BF_4^-$, $OS(O)_2CF_3$, $PF_6^-$, $SbF_6^-$, and $ClO_4^-$.

8. The process according to claim 7, wherein:
(1) the step of reacting is optionally performed in a solvent selected from the group consisting of dichloromethane, tetrahydrofuran, 2-methyltetrahydrofuran, methanol, ethanol, trifluoroethanol, isopropanol, ethyl acetate, and isopropyl acetate, or a mixture thereof; or
(2) the hydrogen gas is present at a pressure of 20 bar or less; or
(3) $L_1$ is a pair of identical alkene ligands selected from the group consisting of ethylene, cyclooctene, and norbornene; or
$L_1$ is a pair of identical solvent ligands selected from the group consisting of acetonitrile, tetrahydrofuran, 2-methyltetrahydrofuran, methanol, ethanol, trifluoroethanol, and isopropanol; or
$L_1$ is a bidentate ligand selected from the group consisting of 1,5-cyclooctadiene (COD), 1,5-hexadiene, and norbornadiene; and
$L_2$ is a pair of identical alkene ligands selected from the group consisting of ethylene, cyclooctene, and norbornene; or
$L^2$ is a pair of identical solvent ligands selected from the group consisting of acetonitrile, tetrahydrofuran, 2-methyltetrahydrofuran, methanol, ethanol, trifluoroethanol, and isopropanol; or
$L_2$ is a bidentate ligand selected from the group consisting of 1,5-cyclooctadiene (COD), 1,5-hexadiene, and norbornadiene; or (4) the hydrogenation catalyst comprises $[Rh(L_1)(L_2)]^+ BF_4^-$ wherein:

(a) $L_1$ is a pair of monodentate ligands, wherein the pair of monodentate ligands is a pair of identical alkene ligands or a pair of identical solvent ligands; or $L_1$ is a bidentate ligand, wherein the bidentate ligand is a diene ligand; and (b) $L_2$ is or (CAS # 565184-29-4)

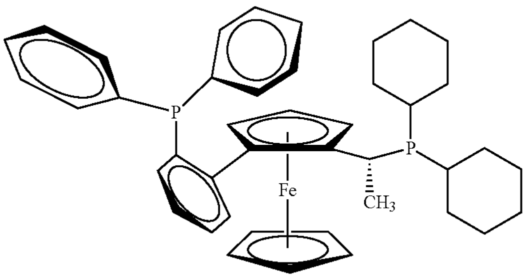

;

(5) the hydrogenation catalyst comprises $[Rh(L_1)(L_2)]^+ BF_4^-$ wherein:

(a) L is a pair of monodentate ligands, wherein the pair of monodentate ligands is a pair of identical alkene ligands or a pair of identical solvent ligands; or $L_1$ is a bidentate ligand, wherein the bidentate ligand is a diene ligand; and (b) $L_2$ is or (CAS # 849925-29-7)

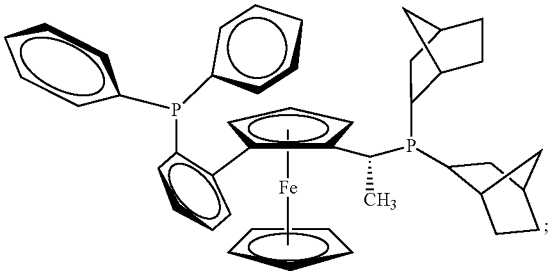

;

(6) the rhodium pre-catalyst is $[Rh(COD)_2]^+BF_4^-$; or (7) the compound of Formula I has an enantiomeric excess of the (R)-enantiomer of at least 90%; or (8) the compound of Formula I has an enantiomeric excess of the (R)-enantiomer of at least 95%; or (9) the compound of Formula I has an enantiomeric excess of the (R)-enantiomer of at least 97%.

9. The process according to claim 8, wherein the step of reacting is performed in a solvent selected from the group consisting of dichloromethane, tetrahydrofuran, 2-methyltetrahydrofuran, methanol, ethanol, trifluoroethanol, isopropanol, ethyl acetate, and isopropyl acetate, or a mixture thereof.

10. The process according to claim 8, wherein the hydrogen gas is present at a pressure of 10 bar or less.

* * * * *